United States Patent
Yamasaki et al.

(10) Patent No.: US 7,175,815 B2
(45) Date of Patent: Feb. 13, 2007

(54) FAN TYPE CHEMICALS DIFFUSING DEVICE

(75) Inventors: Satoshi Yamasaki, Hiroshima (JP); Kazunori Yamamoto, Hiroshima (JP); Atsushi Matsuda, Hiroshima (JP)

(73) Assignee: Fumakilla Ltd., Tokyo (JP)

( * ) Notice: Subject to any disclaimer, the term of this patent is extended or adjusted under 35 U.S.C. 154(b) by 616 days.

(21) Appl. No.: 10/181,573

(22) PCT Filed: Jan. 30, 2001

(86) PCT No.: PCT/JP01/00610

§ 371 (c)(1),
(2), (4) Date: Jul. 18, 2002

(87) PCT Pub. No.: WO01/65931

PCT Pub. Date: Sep. 13, 2001

(65) Prior Publication Data

US 2003/0044326 A1    Mar. 6, 2003

(30) Foreign Application Priority Data

| Mar. 6, 2000 | (JP) | ............................. P2000-059867 |
| Apr. 12, 2000 | (JP) | ............................. 2000-110348 |
| Apr. 12, 2000 | (JP) | ............................. 110326 |
| Apr. 27, 2000 | (JP) | ............................. 2000-127749 |

(51) Int. Cl.
*B01F 3/04* (2006.01)
(52) U.S. Cl. .................... 422/124; 422/122; 422/120; 261/31
(58) Field of Classification Search ............ 422/123, 422/124, 5, 305, 120, 122; 239/34, 53, 60, 239/44; 261/DIG. 65, 31, 84; 96/222
See application file for complete search history.

(56) References Cited

U.S. PATENT DOCUMENTS 4,228,124 A    10/1980    Kashihara et al.

(Continued)

FOREIGN PATENT DOCUMENTS

JP    53-14329    2/1978

(Continued)

OTHER PUBLICATIONS

English language International Preliminary Examination Report dated Nov. 28, 2002 of International Application No. PCT/JP01/00610 filed Jan. 30, 2001; Applicants: Fumakilla Limited et al.

*Primary Examiner*—Krisanne Jastrzab
*Assistant Examiner*—Sean E. Conley
(74) *Attorney, Agent, or Firm*—Frishauf, Holtz, Goodman & Chick, P.C.

(57) ABSTRACT

A fan type chemical diffusing apparatus includes an apparatus main body having an air inlet and an air outlet, a fan type blower disposed in the apparatus main body, and an active ingredient impregnated body or mass for containing an active ingredient. The fan type blower includes a fan casing, a motor, and a fan including a rotary disk and a plurality of blades fastened to a peripheral portion of the rotary disk and provided with a hollow space that is on an interior of the fan with respect to the blades. The fan type blower is operable to send air from the air inlet through the hollow space and out through the air outlet.

11 Claims, 7 Drawing Sheets

U.S. PATENT DOCUMENTS

| | | | |
|---|---|---|---|
| 4,301,095 A * | 11/1981 | Mettler et al. | 261/30 |
| 4,330,506 A | 5/1982 | Takei | |
| 5,282,334 A | 2/1994 | Kimura et al. | |
| 5,335,446 A | 8/1994 | Shigetoyo | |
| 5,431,885 A * | 7/1995 | Zlotnik et al. | 422/122 |
| 5,480,591 A * | 1/1996 | Lagneaux et al. | 261/30 |
| 5,566,502 A | 10/1996 | Shigetoyo | |
| 5,922,093 A * | 7/1999 | James et al. | 55/322 |
| 6,102,660 A * | 8/2000 | Lee | 416/146 R |
| 6,151,827 A | 11/2000 | Smith et al. | |
| 2003/0044326 A1 | 3/2003 | Yamasaki et al. | |

FOREIGN PATENT DOCUMENTS

| | | | |
|---|---|---|---|
| JP | 56-090004 A | | 7/1981 |
| JP | 58-52201 A | * | 3/1983 |
| JP | 61-182273 U | | 11/1986 |
| JP | 64-7925 A | * | 1/1989 |
| JP | 03-151305 A | | 6/1991 |
| JP | 5-68459 A | | 3/1993 |
| JP | 6-75179 U | | 10/1994 |
| JP | 7-111850 A | | 5/1995 |
| JP | 8-147 A | | 1/1996 |
| JP | 8-154554 A | | 6/1996 |
| JP | 08-310907 A | | 11/1996 |
| JP | 10-7507 A | | 1/1998 |
| JP | 10-191862 A | * | 7/1998 |
| JP | 11-28040 A | | 2/1999 |
| JP | 11-504627 A | | 4/1999 |
| JP | 11-169051 A | | 6/1999 |
| JP | 11-308955 A | | 11/1999 |
| JP | 2000-023612 A | | 1/2000 |
| JP | 2000-063329 A | | 2/2000 |
| JP | 2000-139319 A | | 5/2000 |
| JP | 2000-189032 A | | 7/2000 |
| JP | 2000-198702 A | | 7/2000 |
| JP | 6-4393 | | 12/2003 |
| WO | WO96/04786 A1 | | 2/1996 |

* cited by examiner

FAN TYPE CHEMICALS DIFFUSING DEVICE

TECHNICAL FIELD

The present invention relates to a fan type chemical diffusing apparatus of volatilizing a chemical, a technique for diffusing an active ingredient of a volatile chemical such as an insecticide, insect repellent or moth-proofing agent, aromatic chemical and deodorant by ventilating a carrier body impregnated with the active ingredient while utilizing a fan type blower powered by a motor.

More specifically, the invention relates to a fan type debugging apparatus for repelling and exterminating or excluding noxious or harmful insects including bugs such as mosquitoes, flies, cockroaches, mites, ants and centipedes and clothing bags such as skin beetles and clothes moths by ventilating a carrier body impregnated with an active ingredient while using a fan type blower powered by a motor energized by a battery or cells.

BACKGROUND ART

A fan type chemical volatilizing and diffusing apparatus has been known which is designed to diffuse into the atmosphere, e.g., in a room an active ingredient of a volatile chemical such as an insecticide, insect repellent or moth-proofing agent, aromatic chemical and deodorant by the force of a wind.

This typical fan type chemical volatilizing and diffusing apparatus is provided with an air inlet for admitting air from the outside into the apparatus body and an air outlet for sending out air admitted. In the air flow passage between the air inlet and the air outlet there are mounted a fan type blower driven by a motor and an active ingredient carrier body impregnated with an active ingredient. Provided also in the apparatus body is a room for accommodating a battery for powering the motor and hence the fan blower.

The active ingredient impregnated body is disposed either in the air flow passage between the air inlet and the fan or in the air flow passage between the fan and the air outlet. Thus, the apparatus is of the type in which rotating the fan to send air causes the active ingredient in the impregnated body to diffuse through the air outlet into the atmosphere.

As shown in JP U H06-4393A, another fan type chemical diffusing apparatus has been known in which the fan in a fan type blower itself contains a volatile chemical.

The typical fan type chemical diffusing apparatus mentioned above is provided with the fan type blower and the active ingredient impregnated body separately in the apparatus body and formed with an air flow passage in the apparatus body. As a result, it is forced to be complex in structure and makes the apparatus large in size.

The requirement that the active ingredient impregnated body and the fan be arranged to efficiently send air into, through and out of the active ingredient impregnated body tends to make the apparatus structure complex and large in size.

If the apparatus is to be powered by a battery, providing a space for accommodating the battery in the apparatus makes the apparatus even more complex and larger in size.

It should be noted in particular that the site in which the active ingredient impregnated body is placed determines the size of the apparatus and a degree of its complexity.

The fan type chemical diffusing apparatus disclosed in JP U H06-4393A by having the fan effectively functioning as the active ingredient impregnated body seeks to resolve the problem of how it can efficiently be arranged and to simplify the apparatus structure. However, many problems still remain unresolved, for example, as regards an unsatisfactory durability (e.g., brittleness) of the fan which must be made by forming, a limited impregnable amount (small amount) of an active ingredient and, if the fan is of replacement type, the time, labor and cost entailed for replacement, which may make the apparatus poor in utility and serviceability.

As an example of the fan type chemical diffusing apparatus using a fan type blower, a debugging apparatus of first type for repelling and exterminating or excluding a noxious or harmful insect has also been disclosed which is designed to volatilize a chemical by providing an air flow through the chemical by means of a fan blower driven by a motor. See, for example, JP P S53-14329A, JP U S61-182273A, JP U H06-75179A, WO96/04786, JP P H08-154554A, JP P H11-504627A and JP P H11-28040A.

As another example as disclosed in JP P H05-68459A, a debugging apparatus of second type has also been disclosed in which a volatile chemical is retained within the chemical diffusing fan which may be rotated to volatilize the chemical.

Further, as another example, a third type of debugging apparatus has been known as disclosed in JP P H07-111850A, a third type of debugging apparatus has been disclosed in which a carrier impregnated with a chemical and also functioning to rectify a gas flow is disposed in the air intake side of a fan which may be rotated to cause an air flow created to volatilize the chemical.

The first type debugging apparatus seems to lack concreteness and seems to have many problems to be resolved for practical use.

The second type debugging apparatus is technologically concrete and practical but if ever practiced seems to lack flexibility. A need to make the retainer larger in size in order to volatilize a larger amount of a chemical proportionally increases energy needed to drive the fan.

The third type debugging apparatus is technologically concrete and practical but is noted to require the carrier not only to be larger in area but to have a shape suitable to reduce air resistance as much as possible. As the present inventors' scrutiny indicates, the idea of requiring the active ingredient impregnated body to be larger in area in order to volatilize a larger amount of the active ingredient must be justified. But, the idea of requiring it to be shaped so as to reduce wind resistance as much as possible was found much questionable.

For to remove wind resistance means reducing wind pressure per unit area and this would reduce a force to detach the chemical from the carrier. Then, the phenomenon would take place that the wind passes away from the carrier without enough carrying the chemical, or a reduction in chemical concentration per unit air flow. This is a loss in wind force and in other words a loss in driving energy.

In contrast, excessively increasing air resistance would reduce the wind speed of a wind coming out of the air outlet and lose the capacity to carry the chemical far.

As an example of the debugging apparatus using a fan type blower, a fourth type of such apparatus has also been proposed which is designed to volatilize a chemical by providing an air flow through the chemical by means of a fan blower driven by a motor. See, for example, JP P S53-14329A, JP U S61-182273A, JP U H06-75179A, WO96/04786, JP P H08-154554 and JP P H11-504627A.

Further, as another example, a fifth type of debugging apparatus has also been proposed as disclosed in JP P H11-28040A which comprises a DC motor powered by a battery and a fan to be driven by the DC motor to provide an air flow through a chemical for its volatilization.

The fourth type debugging apparatus seems to lack concreteness for using a battery as power supply and seems to have many problems to be resolved for practical use.

The fifth type debugging apparatus is an apparatus with a battery as power supply and is shown in its second apparatus to have a current consumption of not greater than 100 milliamperes when the DC motor is unloaded. However, no consideration appears to be taken, e.g., in efficiently using the battery to allow the chemical to be volatilized for a prolonged time period.

Thus, a fan type debugging apparatus for repelling and excluding harmful or noxious insects as previously described is used as placed on a storage space in a house in order to run over a long period of time or as carried by a worker for use to run outdoors. It is therefore desirable that the apparatus have the ability to volatilize a chemical for a long time without the need to change the battery.

Another example of the fan type debugging apparatus has also been known as disclosed, for example, in JP P H11-308955A.

This fan type debugging apparatus has an apparatus body provided with a motor, a fan, a battery and a chemical retainer and is operable to provide an air flow through the chemical retainer from the fun by driving the motor with the battery power to volatilize the chemical. It is shown that the motor is intermittently operated to iteratively have a time period of air flow and a time period of halt alternately with the time period of halt being ten times or more as long as the time period of air flow.

The fan type debugging apparatus referred to above is designed for use as placed in a storage space such as a wardrobe or closet and is there found to extend the debugging component enough inside the closed space and capable of maintaining its efficacy enough for a long time.

However, using this type of apparatus as placed in a living space in a dwelling proves it insufficiently efficacious.

There have also bee known chemical volatilizing and diffusing methods using the wind force of a fan to volatilize and diffuse a volatile chemical into the atmosphere. For example, JP U S61-182273A discloses applying a wind from the fan to a chemical impregnated retainer body having a moderate air permeability, and JP P H07-11850A discloses defining a relationship between a fan's wind force and a permeability.

To the present inventors' knowledge, all the chemical impregnated or retainer bodies (active ingredient impregnated bodies) so far proposed in the prior art are bodies which are solidified and monolithic. For this reason, they provide an effective means if chemicals to be carried thereby are high in vapor pressure and thus highly volatile. If a need arises to volatilize a chemical which is less volatile or hard to volatilize or to volatilize a plenty of a chemical at a time, it has become necessary to take a measure such as: (1) to make larger the area of volatilization of a chemical impregnated body; (2) to make larger voids in a chemical impregnated body to facilitate wind passage; and to intensify the fan's output.

It has been found, however, that any of these measure cannot be taken without making larger the entire volume of the chemical impregnated body, or without making the fan larger in size or deteriorating energy efficiency. Especially, an increase of the chemical impregnated body in size brings about the problems as follows:

(1) Local changes in air flow within the chemical impregnated body. Thus, as it becomes distant especially from the wind blow outlet, the air flow per unit time tends to be reduced by an air resistance that develops in the chemical impregnated body. If the chemical impregnated body is larger in the direction of the wind, the wind force which the chemical impregnated body instantaneously receives varies from one site to another. This leads to an unbalance of volatilization over the entire impregnated body and prevents the chemical from volatilizing stably.

(2) Even if the situation (1) develops, stable volatilization will be possible even for the solidified, monolithic chemical impregnated body if the chemical impregnated is quickly made even in the body. However, increase in the size of the chemical impregnated body makes longer the distance for the chemical to move and requires longer time for the chemical to be made even in the body.

(3) An increase in size of the chemical impregnated body for the reason of the problem mentioned at (1) above also brings about a drop in the air flow per unit time from the air outlets (volatilization outlets) of the chemical impregnated body receptacle, which leads to a drop in the ability of the chemical to volatilize into a room and in turn to a drop in the efficacy of the chemical. Made to resolve these problems, an attempt to intensify the fan's wind force is an attempt to waste energy and proves inefficient and uneconomical.

Accordingly, it is an object of the present invention to provide a fan type chemical diffusing apparatus that can resolve one or more of the problems mentioned earlier.

It is also an object of the present invention to provide a fan type debugging apparatus for repelling and exterminating or expelling a noxious or harmful insect that permits an active ingredient to be volatilized in a maximum amount with a minimum input driving energy.

It is also an object of the present invention to provide a fan type debugging apparatus operated with a battery which permit a chemical to be volatilized over a prolonged time period without the need to exchange the battery.

It is also an object of the present invention to provide a fan type debugging apparatus usable in a living space, proving a sufficient efficacy and capable of maintaining the sufficient efficacy for a prolonged time period.

It is also an object of the present invention to provide a chemical volatilizing method that permits a volatile chemical having insecticide, insect repellent or growth control function to be diffused and dispersed stably by a wind force over a prolonged time period for a variety of noxious or harmful insects, regardless of the vapor pressure the chemical possesses and the amount of volatilization the chemical is aimed for.

DISCLOSURE OF THE INVENTION

There is provided in accordance with the present invention in a first form of implementation thereof a fan type chemical diffusing apparatus, characterized in that it comprises: an apparatus main body having an air inlet and an air outlet; a fan type blower disposed in the apparatus main body and having a fan casing, a fan provided with a hollow space, and a motor; and an active ingredient impregnated body or mass disposed in the hollow space for containing an active ingredient, wherein the fan type blower is adapted and operative to send air from the air inlet through the hollow space into and out of the air outlet.

This first form of implementation of the present invention that requires that a fan be uniquely provided with a hollow space adapted to accommodate therein an active ingredient impregnated body or mass only requires the apparatus body portion to have a space therein just enough to accommodate the fan blower, and eliminates the conventional need to provide an extra space for separately accommodating an active ingredient impregnated body.

This simplifies the apparatus body interior structurally and makes the apparatus compact and small sized.

Also, eliminating the requirement to dispose the active ingredient impregnated body beside the fan blower in the body portion of the apparatus, it enhances its design flexibility.

Also, the fan is found not to reduce its durability and capable of retaining a sufficient amount of an active ingredient.

In the construction stated above, the active ingredient impregnated body or mass is preferably fixed to one of the said fan casing and the apparatus main body.

This specific construction permits the active ingredient impregnated body or mass to be placed as non-rotatable with the fan and to be kept not to increase the rotational resistance of the fan, and thus not to create a waste in its driving force.

In the construction stated above, the active ingredient impregnated body or mass is preferably mounted removably in the hollow space.

This construction makes the apparatus economical because it then requires only the active ingredient impregnated body or mass to be exchanged while leaving the fan intact.

Extensive and zealous investigations and experiments conducted by the present inventors with what have been stated hereinbefore taken into consideration have revealed that there is a delicate balancing relationship between wind resistance and amounts of volatilization of an active ingredient and has led them to the form of implementation of the invention mentioned below.

Thus, in accordance with a second form of implementation of the present invention there is provided a fan type debugging apparatus for repelling and excluding or expelling a noxious or harmful insect with an active ingredient containing as its principal component at least one chemical having a vapor pressure of not less than $1.0 \times 10^{-4}$ mmHg at a temperature of 30° C. and effective to act as an insecticide or acaricide or to control growth, or to hinder bloodsucking, biting or eating behavior, of the insect, or to repel the insect, or effective to prevent any other damage by the insect, the apparatus having an active ingredient impregnated body or mass adapted to retain and release by volatilization the active ingredient, and including a fan type blower powered to be driven by a motor, characterized in that: the said active ingredient impregnated body or mass is disposed in a wind inlet side of the said fan type blower and is designed to provide a wind force resistance R which in terms of the proportion of current consumption E2 by the said motor in the presence of the said active ingredient impregnated body or mass to current consumption E1 by the said motor in the absence of the said active ingredient impregnated body or mass, ranges from 5 to 25% where R is expressed by the equation: $R=100-E2/E1 \times 100$.

This second form of implementation of the present invention enables a motor driving energy to be efficiently utilized to volatilize a plenty of active ingredients, and provides volatilization of a maximum amount of the active ingredient and thus a maximum extent of vermin or insect damage prevention at a minimum amount of input energy.

In order to achieve the object or objects mentioned before, extensive investigations and experiments conducted by the present inventors in variously changing fan's air resistance index, fan size and weight and motor parameters have led them to the following form of implementation of the invention.

Thus, in accordance with a third form of implementation of the present invention there is provided a fan type debugging apparatus for repelling and excluding a noxious or harmful insect with an active ingredient containing as its principal component at least one chemical having a vapor pressure of not less than $1.0 \times 10^{-4}$ mmHg at a temperature of 30° C. and effective to act as an insecticide or acaricide or to control growth, or to hinder bloodsucking, biting or eating behavior, of the insect, or to repel the insect, or effective to prevent any other damage by the insect, the apparatus having an active ingredient impregnated body or mass adapted to retain and release by volatilization the said active ingredient, and including a fan type blower powered to be driven by a motor which is in turned by a battery, characterized in that the said fan type blower comprises a fan having: an air resistance f which when expressed by current consumption $I_1$ by the said motor loaded with the said fan divided by current consumption $I_0$ by the said motor when unloaded with the said fan, ranges not less than 1 but not greater than 17; a size in a range between 20 mm and 100 mm in diameter; and a weight in a range between 1.5 gram and 8 grams, wherein values of the said fan air resistance, size and weight are selected as aforesaid and further so that the current consumption by the said motor loaded with the said fan has a current value such that the ratio of a time period in which the said fan can be driven by the said battery to the capacity of the said battery is not less than 5%.

This third form of implementation of the present invention permits a motor to be driven effectively to ventilate an active ingredient impregnated body or mass for a prolonged gross time period without the need to exchange a battery and thus the active ingredient to be volatilized for such a long gross period without the need to replace the battery for.

The failure of the conventional fan type debugging apparatus if used as placed in a living space to yield enough efficacy as mentioned herein earlier was reasoned by the present inventors as follows:

In contrast to a wardrobe or closet in which the conventional fan type debugging is usable as placed and which is opened or closed usually only twice or so a day in the morning and evening, a living space has a number of visitors and is opened and closed frequently a day, and hence has air entry and exit much more than the storage space.

For this reason, making the time period in which the air flow is halted so long as ten times longer than the time period in which air is driven to flow prevents the debugging agent (active ingredient) from spreading and diffusing enough to an extent that a satisfactory efficacy is obtained.

Extensive and zealous investigations and experiments conducted by the present inventors with these reasons taken into consideration have led them to the following form of implementation of the invention:

Thus, in accordance with a fourth form of implementation of the present invention there is provided a fan type debugging apparatus for repelling and excluding a noxious or harmful insect with an active ingredient containing as its principal component at least one chemical having a vapor pressure of not less than $1.0 \times 10^{-4}$ mmHg at a temperature of 30° C. and effective to act as an insecticide or acaricide or to control growth, or to hinder bloodsucking, biting or eating behavior, of the insect, or to repel the insect, or effective to prevent any other damage by the insect, the apparatus having an active ingredient impregnated body or mass adapted to retain and release by volatilization the said active ingredient, and including a fan type blower powered to be driven by a motor, characterized in that: the said fan type blower is operable to iteratively run and halt alternately with a time period of halt not more than 9 (nine) times as long as a running time period, the said time period of halt being also a time period in which a current or quantity of electricity not lost therein is more than a current or a quantity of electricity consumed in excess by the said motor in the said running time period.

This fourth form of implementation of the present invention permits an apparatus if used as placed in a living space to provide a sufficient efficacy and to retain this efficacy for a prolonged period of time.

In a construction as stated above, desirably:

The said active ingredient impregnated body or mass comprises a mass of discrete particles impregnable with the said active ingredient and the said particles each have a shape such that a maximum area of contact with one particle with another is not larger than one half of a total surface area thereof;

The said active ingredient impregnated body or mass comprises a mass of discrete particles impregnable with the said active ingredient and the said particles have a real volume which as expressed by [apparent volume×(1−percentage of void or voids/100)] ranges from $5 \times 10^{-5}$ to $5 \times 10^{5}$ mm$^3$ per particle.

The said fan type blower is adapted to send air into, through and out of the said active ingredient impregnated body or mass receptacle which comprises an active ingredient impregnated mass of discrete particles with an air flow therethrough ranging between 0.01 and 1.0 m$^3$/min., and the said particles then have a specific gravity ranging between 0.005 and 0.5; and/or At least one of the said active ingredient impregnated body or mass and a receptacle therefor is pre-treated for an antistatic.

These and other features, objects and advantages of the present invention will become more readily apparent to those of ordinary skill in the art from the following detailed description of the preferred forms of embodiment thereof as illustrated in the various drawing Figures.

BEST MODES FOR CARRYING OUT THE INVENTION

An explanation is first given in respect of an apparatus according to the first form of embodiment of the present invention.

Figure 1:
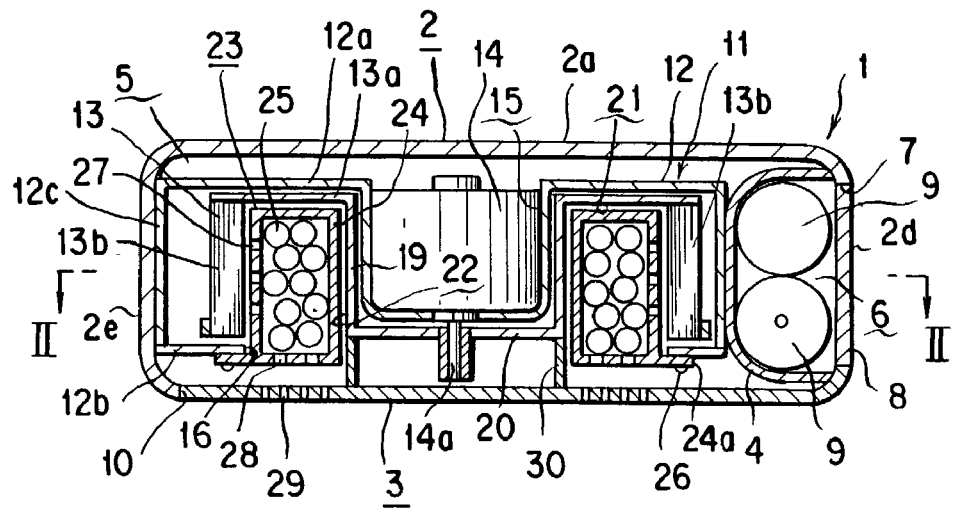
FIG. 1 is a longitudinal cross sectional view that diagrammatically depicts a fan type chemical volatilizing diffusing apparatus according to a first form of embodiment of the present invention.
Figure 2:
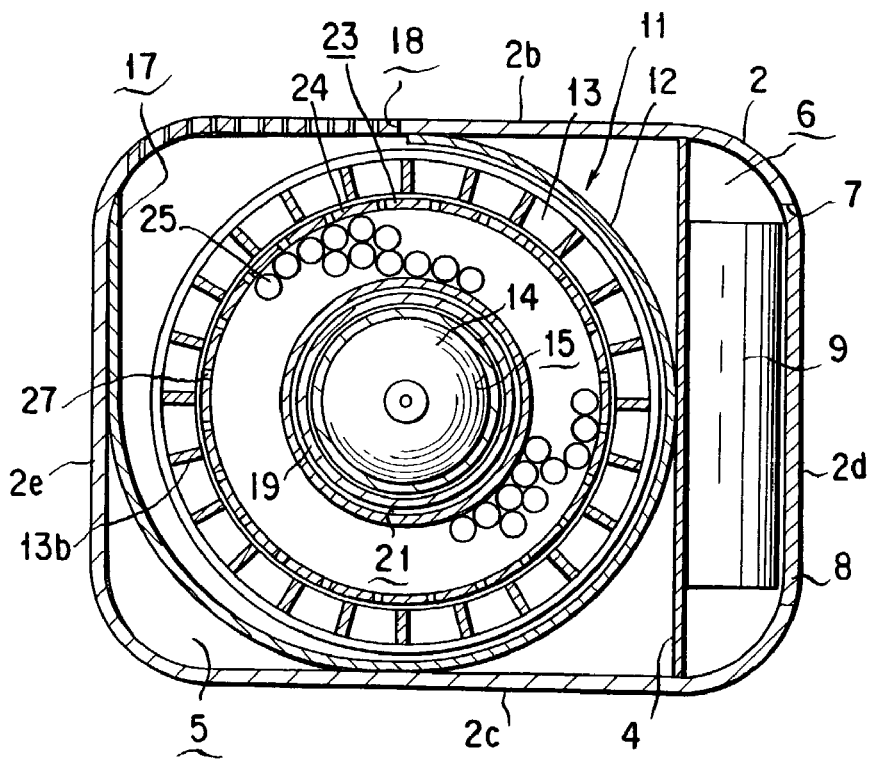
FIG. 2 is a transverse cross sectional view of the apparatus taken along the lines II—II as viewed in the direction indicated by the arrows in FIG. 1.

As shown in FIGS. 1 and 2, the apparatus comprises an apparatus main body or body portion 1 which as a whole is in the form of a substantially rectangular box having its one side portion 2 and its other side portion 3.

The first side portion 2 is made up of a substantially rectangular side face plate 2a and a first, a second, a third and a fourth end face plate 2b, 2c, 2d and 2e which are continuous with the peripheral portion of the side face plate 2a. The first side portion 2 is thus in the form of a substantially rectangular box with one side face open. Disposed between the first and second end face plates 2b and 2c which are opposed to each other and lying closer to the third end face plate d is a partition plate 4 fastened thereto, whose horizontal cross section is shaped substantially in the form of letter "U", and which subdivides the apparatus body portion 1 into a fan type blower accommodating chamber 5 and a battery chamber 6.

The third end face plate 2d is formed with an opening 7 shown as closed with a cover 8 for putting dry cells 9 in and out of the battery chamber 6 by opening the cover 8.

The other side portion 3 is planar and is removably attached to an opening 10 formed by the first, second, third and fourth end face plates 2b, 2c, 2d and 2e. The other side portion 3 is so attached, e.g., in a snap fit or in a hinged door fit.

A fan type blower 11 is shown disposed in the fan type blower accommodating chamber 5 and comprises a fan casing 12, a fan 13 and an electric motor 14.

The fan casing 12 which comprises its one side face plate 12a, other side face plate 12b and peripheral face plate 12c has a recess 15 formed in a center region of the one side face plate 12a so as to sink towards the opening 10 to hold the motor 14 therein. The other side face plate 12b is formed with a large diameter hollow 16 which is toroidal.

The peripheral face plate 12c is formed with a discharge or delivery outlet 17 which is continuous with an air outlet 18 formed in the first end face plate 2b.

The fan 13 is configured in the form of a centrifugal fan, comprising a rotary disk 13a and a large number of radially extending blades 13b fastened thereto closer to its periphery. The rotary disk 13a is formed closer to its center with a cylindrical and a planner portion 19 and 20 forming a hollow that sinks towards the large diameter hollow 16, and providing an annular hollow space 21 between the cylindrical portion 19 and the blades 13b. The hollow space 21 is open to communicate with the atmosphere via an intake opening 22 between the large diameter hollow 16 of the other side face plate 12b and the cylindrical portion 19.

The motor 14 has its drive shaft 14a connected to the planar portion 20 of the fan 13 and is driven to rotate the fan 13.

Unloadably loaded in the hollow space 21 of the fan 13 is a cartridge-type active ingredient or a carrier body or mass 23 for the active ingredient.

The active ingredient carrier body or mass 23 includes a housing 24 that is hollow and toroidal in which a large number of particulate or granular processed goods 25 of active ingredient are contained. In loading the body 23, the housing 24 may be inserted from the intake opening 22 into the hollow space 21 and then fixed in position by fastening attachment pieces 24a provided for the housing 24 to the other side face plate 12b of the fan casing 12 by means of machine screws 26.

The housing 24 is formed with a large number of air outlets 27 opposed to the blades 13b and air inlets 28 which are opposed to air intake ports 29 formed in the other side portion or member 3. The other side member 3 is provided with an airflow guide 30.

In operation, rotating the fan 13 by the motor 14 causes air to be drawn from the atmosphere through the intake ports 29 and the air inlets 28 into the housing 24 and, ventilating the particulate processed goods 25, allows the chemical to volatilize and then spread into the atmosphere through the air outlets 27, the discharge outlet 17 and the air outlet port 18.

Then, with the active ingredient impregnated body or mass 23 itself non-rotated, the fan 13 is prevented from increasing its rotational resistance.

Also, the ability to take the active ingredient impregnated body or mass 23 out of the hollow space 21 into the outside of the apparatus body portion 1 by removing the other side member 3 and loosening the machine screws 26 allows the active ingredient impregnated or carrier body or mass 23 to be exchanged as desired.

An explanation is next given in respect of modifications of the first form of embodiment of the invention.

Thus, first with respect to the direction of ventilation, while in the form of embodiment described above air is drawn through a lower surface to flow out through a side surface of the fan type blower 11 with its axis of rotation (i.e., the drive shaft 14a of the motor 14) set to extend vertically, as an alternative air can be, e.g., drawn through one side surface to flow out through another side surface, or drawn through an upper surface to flow out through a side surface of the fan type blower 11 with the air inlet and outlet ports 29 and 18 properly rearranged.

Likewise, the form of the apparatus can be altered according to its aimed use. For example, it is possible to set the axis of rotation of the fan type blower 11 (i.e., the drive shaft 14a of the motor 14) to extend in a transverse (front and rear) direction, thus to make the apparatus longer vertically and suitable for placement in a vertical clearance.

For the fan 13 of the fan type blower 11 for use in the present invention, in order to change the air flow from an axial direction to a radial direction, use is made of a centrifugal fan in which a centrifugal force is applied to impart an energy to the flow.

A centrifugal fan is preferable for the fan 13 because it has a large number of blades which are wider in width and lower in height, and structurally it has no blade but a hollow space in its central area.

A centrifugal fan is preferable also because it is high in blast power and relatively small in size.

Illustrative are, for example, a turbo fan, an airfoil fan, a limited load fan, a radial fan, a multi-blade fan and so on.

It is also preferable that a centrifugal fan as mentioned above be placed in a volute, spiral or scroll casing designed to bring together efficiently winds produced by rotating the fan and then to let them out.

For the active ingredient impregnated body or mass 23 for loading in the hollow space 21 of the above mentioned centrifugal fan, use may also be made of processed goods or a formed body or bodies which can be impregnated with a volatile chemical as an active ingredient.

Illustrative are, for example, processed goods so as to have an active ingredient coated thereon by spraying or the like, or such processed goods accommodated in air-permeable housing as in the case of FIGS. 1 and 2, or a formed body or bodies such as of a synthetic resin containing an active ingredient.

No limitation is imposed on materials that may make up the processed goods or formed body except that they must be capable of fully containing an active ingredient and that they must be capable of releasing it when ventilated.

Illustrative for such materials are, for example, pulp, paper such as filter paper or cardboard, a natural fiber such as of cotton, wool or chingma, an artificial fiber such as of polyester, nylon or polyolefine, a carbon fiber, a glass fiber, a ceramic, a synthetic resin such as of polyolefine, polyvinyl chloride or high-oil-absorptive polymer, non-woven fabric, and a porous natural material.

No limitation is imposed on the shape or configuration of the active ingredient impregnated body either, except that the body must be disposed in the hollow space of the centrifugal fan. Illustrative for the shape and configuration are, for example, circular, semicircular, square and polygonal frames, and a toroidal hollow body.

No limitation is imposed on the size or geometry of the active ingredient impregnated body either, except that the body must be readily disposed in that hollow space and that the body must not impair the fan to rotate.

No limitation is imposed on the thickness or length of the active ingredient impregnated body either, which relates to the content of the active ingredient impregnant, except that it may be sized to meet with its aimed use. The body may even be designed to have its length in excess of the length of the hollow space.

Also, as for loading the active ingredient impregnated body or mass, while in the form of embodiment described the housing 24 in which particulate processed goods 25 as the active ingredient impregnated body are packed is shown to be inserted into the hollow space 21 in the centrifugal fan 13 and to be fastened to the fan casing 21, such a housing 24 may be fastened directly to the apparatus main body portion 1, e.g., by means of a clamping plate as separately prepared. It is also possible to provide the apparatus main body portion 1 with an opening for insertion (e.g., in a region of the air intake port 29 in the other side portion 3) so that the housing 24 may be inserted therethrough and then fastened so.

Also, the fastening means is not limited to a machine nut or nuts but may adopt an adhesive or cladding means. It is preferable that any such means be selected according to the particular form of the active ingredient impregnated body designed for its intended use.

Also, illustrative for the battery or cell 9 used to power driving the fan type blower 11 are, for example, a primary cell or battery such as an alkaline dry cell, a manganese dry cell, a button type cell, an air cell or lithium ion cell, and a secondary cell or battery such as a nickel cadmium battery or a lithium ion cell.

A suitable choice of a particular cell or battery may be made in conjunction with its kind (e.g., either alkaline or manganese, or unit 1 or unit 2 type), its number and its manner of connection (parallel or series) in consideration of its use conditions and period, the kind of the motor and fan used.

The fan type blower 11 for driving may also be powered by the commercial AC supply (e.g., with 100 volts). Then, it will become necessary to provide the apparatus internally or externally with an AC-DC converter.

Also, a fan type chemical diffusing apparatus according to the present invention is not limited to a dedicated or exclusive apparatus as shown in FIGS. 1 and 2 but may be applied to any home or office electrical appliance using a centrifugal fan as well, to provide it with the capability of repelling and exterminating noxious or harmful insects, deodorizing an offensive odor, and emanating fragrance or aroma.

The present invention, if implemented into, e.g., a battery type portable apparatus that has no particular limitation on the place of installment or that can be used anywhere is found to be useful and advantageous.

Illustrative for the volatile chemical for use in the present invention are included, among a variety of chemicals, an insecticide, an insect repellent, an aromatic and a deodorant.

The insecticides should preferably be pyrethroid insecticides of which at least one chemical selected from the group which consists of terallethrin, prallethrin, furamethrin, allethrin, and empenthrin may be used as particularly advantageous.

For growth control (inhibiting) agents, at least one chemical may be used as preferred which is selected from the group consisting of pyriproxyfen, methoprene and hydroprene.

Also, compounding an anti-oxidizing agent and/or an ultraviolet absorbing agent into the active ingredient impregnated body and/or compounding an ultraviolet absorbing agent into a casing for the active ingredient impregnated body will enable an implementation of the present invention to be used stably for a prolonged period of time. It also enables use in the outdoors.

End point marking methods which are essential to the preparation of a chemical include a method of using a lipophilic anthraquinone dye for the impregnated body if hydrophilic and utilizing the phenomena that the color of the dye if dissolved in the chemical is recognizable and that when the chemical is evaporated out the dye gets into the body to make its color unrecognizable. Also included is a method of utilizing a color changeable pigment made of a color changeable electron releasing organic compound and a desensitizer, or a color changeable electron releasing organic compound, a desensitizer and a color developer. Further included is a method in which the rate of sublimation of a subliming agent is made substantially equal to the rate of volatilization of the chemical. While any one of these methods may be used singly, the use of a change in color and a subliming agent in combination will make one feel the use actually and thus would be preferred.

The rate of sublimation can be adjusted at a value as required by adjusting the area of a vent opening that may be provided for a casing containing the subliming agent.

Also for the active ingredients described, there is no limitation imposed in using the insecticides and/or rejectants (insect repellents) listed below, in any combination with a proportion as desired.

For example, in killing insects, any one or more of a variety of volatile insecticides so far used may be utilized. Illustrative are pyrethroid insecticides, carbamate insecticides and organophosphorus insecticides. Pyrethroid insecticides are known to be high in safety and have been used well, of which preferred examples are listed below, each given in the order of the general name, the chemical name and the parenthesized trade name followed by the producer.

allethrin: d1-3-allyl-2-methyl-4-oxo-2-cyclopentenyl d1-cis/trans-chrysanthemat (Pynamin, Sumitomo Chemical Co.)

d1·d-T80-allethrin: d1-3-allyl-2-methyl-4-oxo-2-cyclopentenyl d-cis/trans-chrysanthemat (Pynamin forte, Sumitomo Chemical Co.)

d1·d-T-allethrin: d1-3-allyl-2-methyl-4-oxo-2-cyclopentenyl d-trans-chrysanthemat (Bioallethrin)

d·d-T-allethrin: d-3-allyl-2-methyl-4-oxo-2-cyclopentenyl d-trans-chrysanthemat (Esbiol)

d·d-T80-prallethrin: (+)-2-methyl-4-oxo-3-(2-propionyl)-2-cyclopentenyl (+)-cis/trans-chrysanthemat (Etoc, Sumitomo Chemical Co.)

resmethrin: 5-benzyl-3-furylmethyl d1-cis/trans-chrysanthemat (Chrythron, Sumitomo Chemical Co.)

d1·d-T80-resmethrin: 5-benzyl-3-furylmethyl d-cis/trans-chrysanthemat (Chrythron forte, Sumitomo Chemical Co.)

empenthrin: 1-ethynyl-2-methyl-2-pentenyl d1-cis/trans-3-(2,2-dimethyl vinyl)-2,2-dimethyl-1-cyclopropane carboxylate (Vaporthrin, Sumitomo Chemical Co.)

terallethrin: d1-3-allyl-2-methyl-4-oxo-2-cyclopentenyl-d1-cis/trans-2,2,3,3-tetramethyl-cyclopropane carboxylate (Knoxthrin, Sumitomo Chemical Co.)

phthalthrin: N-(3,4,5,6-tetrahydrophthalimide)-methyl d1-cis/trans-chrysanthemat (Neopynamin, Sumitomo Chemical Co.)

d1·d-T80-phthalthrin: (1,3,4,5,6,7-hexahydro-1,3-dioxo-2-indolyl) methyl d1-cis/trans-chrysanthemat (Neopynamin forte, Sumitomo Chemical Co.)

furamethrin: 5-propargyl-2-furylmethyl d-cis/trans-chrysanthemat (PynaminD, Sumitomo Chemical Co.)

permethrin: 3-phenoxybenzyl d1-cis/trans-3-(2,2-dichlorovinyl)-2,2-dimethyl-1-cyclopropane carboxylate (Eksmin, Sumitomo Chemical Co.)

phenothrin: 3-phenoxybenzyl d-cis/trans-chrysanthemat (Sumithrin, Sumitomo Chemical Co.)

imiprothrin: 2,4-dioxo-1-(prop-2-inyl)-imidazolidine-3-yl methyl (IR)-cis/trans-chrysanthemat (Pralle, Sumitomo Chemical Co.)

fenvalerate: α-cyano-3-phenoxybenzyl-2-(4-chlorophenyl)-3-methyl butylate (Sumicidin, Sumitomo Chemical Co.)

cypermethrin: α-cyano-3-phenoxybenzyl d1-cis/trans-3-(2,2-dichlorovinyl)-2,2-dimethyl cyclopropane carboxylate (Agrothrin, Sumitomo Chemical Co.)

cyphenothrin: (±) α-cyano-3-phenoxybenzyl (+)-cis/trans-chrysanthemat (Gokilaht, Sumitomo Chemical Co.)

ethofenprox: 2-(4-ethoxyphenyl)-2-methyl propyl-3-phenoxybenzyl ether (Trebon)

tefluthrin: 2,3,5,6-tetrafluoro-4-methyl benzyl-3-(2-chloro-3,3,3-trifluoro-1-propenyl)-2,2-dimethyl-1-cyclopropane carboxylate fenpropathrin: α-cyano-3-phenoxybenzyl cis/trans-2, 2,3, 3-tetramethyl cyclopropane carboxylate fenfluthrin: 2,3,4,5,6-pentafluorobenzyl-d1-cis/trans-3-(2,2-dichlorovinyl)-2,2'-dimethyl-1-cyclopropane carboxylate 1-ethynyl-2-methyl-2-pentenyl cis/trans-2,2,3,3-tetramethyl-1-cyclopropane carboxylate For specific examples of the organophosphorus insecticides may be listed the following:

diazinon: (2-isopropyl-4-methyl pyrimidil-6)-diethyl thiophosphate (Diazinon)

fenitrothion, MEP; O,O-dimethyl-O-(3-methyl-4-nitrophenyl) thiophosphate (Sumithion)

pyridaphention; O,O-dimethyl-O-(3-oxo-2-phenyl-2H-pyridazin-6-yl) phosphorothioate (Ofunack)

malathion: dimethyl dicarbetoxy ethyl dithiophosphate (Malathon)

dipterex: O,O-dimethyl-2,2,2-trichloro-1-hydroxyethyl phosphonate chlorpyrifos: O,O-dimethyl-O-(3,5,6-trichlor-2-pyridyl)-phosphorothioate fenthion: O,O-dimethyl-O-(3-methyl-4-methylthio-phenyl)-phosphorothioate (Baytex)

dichlorvos: O,O-dimethyl-2,2-dichlorovinylphosphate (DDVP)

propetamphos: O-[(E)-2-isopropoxycarbonyl-1-methylvinyl]-O-methylethylphosphoramidethioate (Safurotin)

Abate: O,O,O',O'-tetramethyl-O,O'-thiodi-P-phenylene phosphorothioate prothiofos: dithiophosphoric acid O-2,4-dichlorophenyl O-ethyl S-propyl ester (Tokuthion)

phoxim: O,O-diethyl-O-(α-cyano benzylidene amino) thiophosphate

For oxadiazol insecticides may be listed the following:

methoxadiazone: 5-methoxy-3-(2-methoxyphenyl)-O-1, 3,4-oxadiazol-2-(3H)-one (Elemic)

For chloro nicotine insecticides may be listed the following:

imidacloprid: 1-(6-chloro-3-pyridyl methyl)-N-nitro imidazolidin-2-ylideneamine (Admire)

acetamiprid: (E)-$N^1$-[(6-chloro-3-pyridyl) methyl]-$N^2$-cyano-$N^1$-methyl acetone amidine (Mospilan)

According to the apparatus described of the present invention, having the fan 13 configured to provide in its bulk, volume and size a hollow space 21 adapted to accommodate an active ingredient impregnated body 23 only requires the apparatus body portion 1 to have a space therein just enough to accommodate the fan blower 11, and eliminates the conventional need to provide an extra space for separately accommodating the active ingredient impregnated body 23.

This simplifies the apparatus body interior structurally and makes the apparatus compact and small sized.

Also, eliminating the requirement to separately dispose the active ingredient impregnated body beside the fan blower in the body portion 1 of the apparatus, it enhances its design flexibility.

Also, the fan is found not to reduce its durability and capable of retaining a sufficient amount of an active ingredient.

According to the apparatus described of the present invention, the active ingredient impregnated body 23 not rotated with the fan 13 is kept not to increase the rotational resistance of the fan 13, and thus does not create a waste in its driving force.

The apparatus described of the present invention is economical because it requires only the active ingredient impregnated body 23 to be exchanged while leaving the fan 13 intact.

An explanation is next given in respect of a fan type debugging apparatus for repelling and exterminating noxious or harmful insects according to second embodiment of the present invention.

Figure 3:
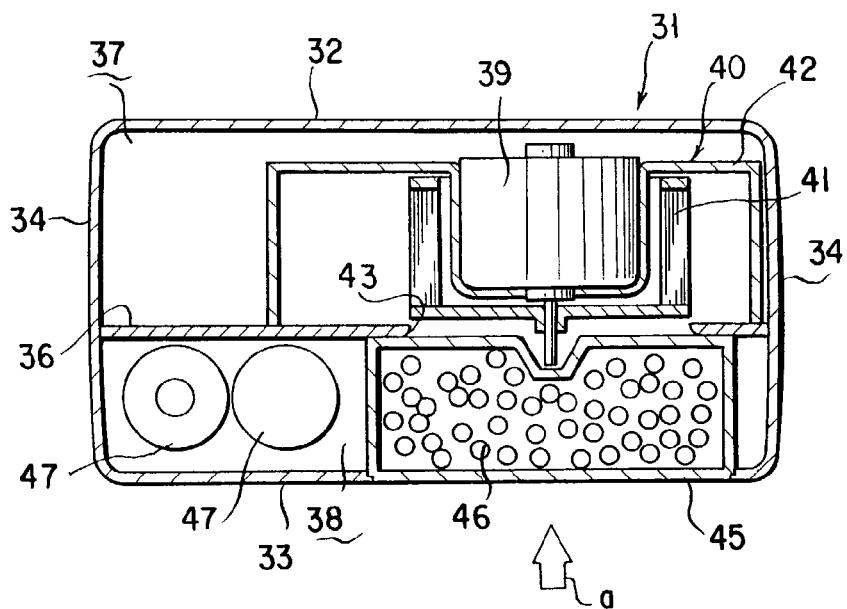
FIG. 3 is a longitudinal cross sectional view that diagrammatically depicts a fan type debugging apparatus for repelling and exterminating noxious or harmful insects according to a second form of the present invention.
Figure 4:
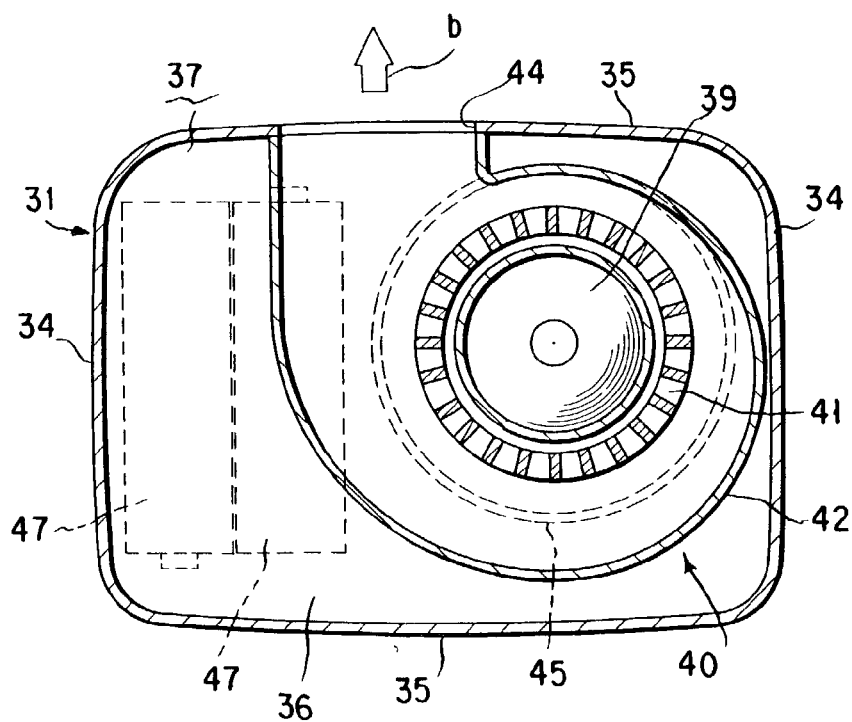
FIG. 4 is a transverse cross sectional view of the debugging apparatus shown in FIG. 3.

Referring to FIGS. 3 and 4, the debugging apparatus has a body portion 31 substantially in the form of a rectangular box, comprising an upper face plate 32, a lower face plate 33, a first pair of opposed side plates 34 and a second pair of side plates 35, defining and enclosing its interior therewith. A partition plate 36 is provided to subdivide with the side face plates 34 and 35, this interior into an upper and a lower space or compartment 37 and 38.

The upper space 37 has a fan type blower 40 mounted therein together with an electric motor 39 for powering the same. The fan blower 40 comprises a fan 41 and a fan casing 42, the latter serving to accommodate and/or to protect the fan 41, and/or to rectify a wind created and/or to intensify the wind force. In the form of embodiment illustrated, the fan 41 is constituted by a silocco fan with the fan casing 42 having its air intake side in communication with an air intake port 43 formed in the partition plate 36 and its outlet side in communication with an air discharge port 44 formed in one of the second pair of side face plates 35.

The lower space 38 has a casing 45 for an impregnated body mounted removably therein as opposed to the air intake port 43.

The impregnated body casing 45 is made of a material and/or has a shape that excels in air permeability to permit air to smoothly pass therethrough.

The impregnated body casing 45 has an active ingredient impregnated body 46 placed therein for accommodation and/or protection thereby.

At least a portion of the impregnated body casing 45 which contacts with the impregnated body 46 is made of plastic comprising at least one of polyester, polypropylene, polyvinyl chloride, ABS, polystyrene, AS, methacrylate resin, polyvinyl alcohol, EVA, phenol resin, silicone resin, polyamide resin, polyacetal resin, polycarbonate resin and thermoplastic polyester resin.

The lower space 38 also has a battery or cells 47 detachably mounted therein, the battery or cells 47 are for driving the motor 39.

In operation, driving the fan 41 with the motor 39 causes air as indicated by the arrow a to be drawn into the fan casing 42 past the impregnated body casing 45, the impregnated body 46 and the intake port 43.

Air drawn into the fan casing 41, creating a wind which is rectified and/or whose wind force is intensified thereby, is allowed to flow out through the outlet port 44 as indicated by the arrow b.

This permits an active ingredient impregnated in the active ingredient impregnated body 46 to volatilize and then through the air outlet port 44 to diffuse into the atmosphere.

In the form of embodiment of the present invention illustrated, for the purposes of convenience a value that may be termed as "wind force resistance value" R is established. In deriving a wind force resistance value, while it may ought to measure the wind (air) speed or air flow quantity direct, a method of measuring the amount of electric current consumption in the motor that varies as the air resistance of the active ingredient would give rise to less measurement error though it is indirect. Accordingly, the latter method is adopted here in the present invention.

The fan type debugging apparatus described should preferably be provided with an impregnated body casing designed to accommodate and/or to protect an active ingredient impregnated body in consideration of performance and stability and in use safety.

Also, the fan blower described should preferably be provided with a fan, a fan casing designed to accommodate and/or to protect the fan, and/or to rectify the wind of air an/or to intensify the wind force of air, and an electric motor.

The active ingredient impregnated body should preferably have a shape or configuration which rather than being a honeycomb form having an air or gas rectifying function is a form of material that is large in effective area which is at least one material selected from the group that consists of a mass of granules, a mass of strips and a mass of strings, filaments or threads. It is also preferable from the standpoints of retention and/or release of the active ingredient that the particulate material forming the active ingredient impregnated body be composed of at least one material selected from the group which consists of a cellulose, a polymeric water absorptive agent, a polymeric oil absorptive agent and a gel.

The active ingredient is preferably an insecticide or a growth control agent that is effective to one or more kinds of insecticides but is not harm to men and beasts.

The insecticides should preferably be pyrethroid insecticides of which at least one chemical selected from the group which consists of terallethrin, prallethrin, furamethrin, allethrin, and empenthrin is particularly advantageous.

For growth control (inhibiting) agents, at least one chemical is preferred which is selected from the group consisting of pyriproxyfen, methoprene and hydroprene.

For the fan as a source that produces a wind force or power, use is preferably made of a silocco fan and/or axial fan configuration. If a silocco fan configuration is used, it is desirable that fan casing is used which is desired to bring winds together around the fan.

In order to exhibit a maximum effect of repelling and exterminating noxious or harmful insects at a minimum energy, use is preferably made of a power saving type motor having a current consumption of 100 mA or less under no load conditions with an applied voltage of 1.5 volts. Also, using a battery or cells as a power supply for such a motor enhances the serviceability of an apparatus according to the invention in the sense that it does not choose a place for installment. The upper limit set at 100 mA or less for permissible current consumption is based on the assumption that a time period of at least 12 hours will be required for use with a unit 3 type cell battery that is high in general-purpose properties.

Also, compounding an anti-oxidizing agent and/or an ultraviolet absorbing agent into the active ingredient impregnated body and/or compounding an ultraviolet absorbing agent into a casing for the active ingredient impregnated body will enable an implementation of the present invention to be used stably for a prolonged period of time. It also enables use in the outdoors.

End point marking methods which are essential to the preparation of a chemical include a method of using a lipophilic anthraquinone dye for the impregnated body if hydrophilic and utilizing the phenomena that the color of the dye if dissolved in the chemical is recognizable and that when the chemical is evaporated out the dye gets into the body to make its color unrecognizable. Also included is a method of utilizing a color changeable pigment made of a color changeable electron releasing organic compound and a desensitizer, or a color changeable electron releasing organic compound, a desensitizer and a color developer. Further included is a method in which the rate of sublimation of a subliming agent is made substantially equal to the rate of volatilization of the chemical. While any one of these methods may be used singly, the use of a change in color and a subliming agent in combination will make one feel the use actually and thus would be preferred.

The rate of sublimation can be adjusted at a value as required by adjusting the area of a vent opening that may be provided for a casing containing the subliming agent.

As a wind or winds created by the rotation of the fan driven by the motor, it is also desirable that air flow in the order of the air intake port, the active ingredient impregnated body, the fan, the fan casing and the air outlet port.

Also for the active ingredients described, there is no limitation imposed in using the insecticides and/or rejectants (insect repellents) listed below, in any combination with a proportion as desired.

For example, in killing insects, any one or more of a variety of volatile insecticides so far used may be utilized. Illustrative are pyrethroid insecticides, carbamate insecticides and organophosphorus insecticides. Pyrethroid insecticides are known to be high in safety and have been used well. Specific examples of the pyrethroid insecticides, the organophosphorus insecticides the oxadiazol insecticides and chloro nicotine insecticides have been listed hereinbefore in connection with the first form of embodiment of the present invention.

For specific examples of the growth control agent may be listed the following:

pyriproxyfen: 4-phenoxy phenyl (RS)-2-(2-pyridyl oxy) propyl ether methoprene: 11-methoxy-3,7,11-trimethyl-2,4-dodecadienoic acid-1-methyl ethyl ester hydroprene: ethyl (2E, 4E)-3,7,11-trimethyl-2,4-dodecadienoate phenoxy carb: ethyl [2-(4-phenoxy phenoxy)ethyl]carbamate For specific examples of the insect repellent may be listed the following:

N,N-diethyl-m-toluamid (deet)
dimethyl phthalate
dibuthyl phthalate
2-ethyl-1,3-hexane diol
1,4,4a,5a,6,9,9a,9b-octa hydrodibenzofuran-4a-carb ardehyde
di-n-propyl isothinchomeronate
p-dichloro benzene
di-n-butyl succinate
diethyl amid caprate
N-propyl acetanilide
β-naphthol
camphor For representative natural volatile oils and their components may be listed the following: citral, citronellal, citronellol, eugenol, methyleugenol, geraniol, cinnamic aldehyde, linalool, perilla aldehyde, nepetalic acid, methylheptanone, decyl aldehyde, myrcene, geraniol acetate, thymol, limonene, cineol, pinene, cymene, terpinene, sabinene, elemene, cedrene, elemol, pidrol, cedrol, hinokithiol, thujaprisin, troporoid, hinokithin, thujopsen, borneol, camphene, terpineol, terpinyl ester, dipentene, phellandrene, caryophyllene, vanillin, furfural, furfuryl alcohol, pinocarveol, pinocarvone, myrtenol, verbenone, carvone, eudesmol, pepritone, thujene, phankyl alcohol, methyl anthranilate, bisabolene, bengaptol (spelled phonetically), nonyl aldehyde, nonyl alcohol, nootkatone, octyl aldehyde, linalyl acetate, geranyl acetate, nerolidol, ocimene, methyl anthranilate, indole, jasmone, benzaldehyde, pulegone, and so forth.

Isomers and/or derivatives of the above

Volatile oils including at least one selected from the above.

In addition to an anti-oxidizing agent and an ultraviolet absorbing agent for preventing degradation of the active ingredient described, there may be incorporated an inhibitor, depressor and/or retardant for adjusting the amount of volatilization of the active ingredient, a substance or substances having a function or functions of giving out fragrance, deodorizing and/or sterilizing as desired in accordance with the present invention.

Next, mention is made of specific examples.

A fan type debugging apparatus as shown in FIGS. 3 and 4 was used. As the active ingredient impregnated body, use was made of two impregnated masses of granules made of cellulose and having diameters of 4 mm and 2 mm, respectively [supplied by Rengo, K. K. under the trade name of Viscopar (spelled phonetically)], and an impregnated mass of strips made of paper cut into a size of 0.3 cm×70 cm. Investigations were made of a relationship between the amount of impregnation or loading and the wind force resistance R values that these bodies were assumed to have as derived from the measured values of current consumption E2 of the motor. The results of the investigations are summarized in Table 1 below. Values of current consumption when the impregnated bodies were unused are shown as E1.

Investigations were also conducted of extents of the knock-down efficacy of these bodies impregnated with an active ingredient for common house mosquitoes and house flies and had results which are also included as efficaciousness in Table 1.

TABLE 1

|  | Impregnated Mass Uninstalled -E1- | Loading Amount (g) | | | | | | | |
| --- | --- | --- | --- | --- | --- | --- | --- | --- | --- |
|  |  | 0.1 | 0.2 | 0.5 | 1.0 | 2.0 | 3.0 | 4.0 | 5.0 |
| Granular Impregnated Mass (4 mm diameter) | | | | | | | | | |
| Current(mA)-E2- | 9.5 | — | — | 9.3 | 8.4 | 8.0 | 7.6 | 7.2 | 6.9 |
| Wind Force Resistance(%) -R- | 0.0 | — | — | 2.1 | 11.6 | 15.8 | 20.0 | 24.0 | 27.8 |
| Efficaciousness | — | — | — | D | B | A | B | B | C |
| Granular Impregnated Mass (2 mm diameter) | | | | | | | | | |
| Current(mA)-E2- | 9.5 | — | — | 8.4 | 7.8 | 7.5 | 7.3 | 7.0 | 6.7 |
| Wind Force Resistance(%) -R- | 0.0 | — | — | 11.6 | 17.9 | 21.1 | 23.2 | 26.3 | 29.3 |
| Efficaciousness | — | — | — | B | A | B | B | C | D |
| Strip-like Impregnated Mass | | | | | | | | | |
| Current(mA)-E2- | 9.5 | 9.1 | 8.6 | 7.8 | 7.3 | 6.9 | — | — | — |
| Wind Force Resistance(%) -R- | 0.0 | 4.2 | 9.5 | 17.9 | 23.2 | 27.8 | — | — | — |
| Efficacious | — | C | B | A | B | C | — | — | — |

Criterion used for the efficaciousness is as shown in Table 2 below. Efficaciousness tests were carried out by leaving an approximately 100 number of sample insects free in a 8.5 straw mat size(14.0 m$^2$) living room, and counting the number of insects knocked down with elapse of time from the commencement of volatilization of the active ingredient. The test results are indicated in KT$_{50}$ values calculated by Bliss' probit method. For the active ingredient, use was made of terallethrin in an amount of loading of 300 mg for one specimen. The criterion for efficaciousness was adopted with reference to results of test likewise done for a heat vaporization liquid agent or a mosquito-repellent incense currently made available in the market.

TABLE 2

| | Efficaciousness | | | |
|---|---|---|---|---|
| | A (Accepted) | B (Accepted) | C (Unaccepted) | D (Unaccepted) |
| Knock-down Efficacy for Common House Mosquitoes $KT_{50}$ (minute) | 0~10 | 10~20 | 20~30 | 30~ |
| Knock-down Efficacy for House Flies $KT_{50}$ (minute) | 0~15 | 15~30 | 30~60 | 60~ |

The fan type debugging apparatus used in the above mentioned investigations and tests had the fan 41 made as a silocco fan directly connected to an electric motor 39 (supplied by Mabuchi Motor Co., Ltd. under the product name RF-330TK-07800) having a current consumption of 4 mA under no load conditions with an applied voltage 1.5 volts, the fan also having a fan casing 42 so disposed as to surround the fan 41. The casing 45 for accommodating an active ingredient impregnated body or mass was disposed on the side of the air intake port 43 to the fan 41. For the battery 47, two unit 3 type alkaline dry cells connected in series are used.

From the results of the investigations and tests mentioned above, it has been determined that if the wind force resistance R of the active ingredient impregnated body or mass 46, namely the proportion of the motor current consumption E2 when the active ingredient impregnated mass 46 is loaded to the motor current consumption E1 when the active ingredient impregnated mass 46 is unused (R=100−E2/E1× 100) is less than 5% or not less than 26%, enough debugging efficacy is not obtainable. However, when that proportion lies in a range of 5 to 25%, it has been found that enough debugging efficacy can be obtained.

The present invention enables a motor driving energy to be efficiently utilized to volatilize a plenty of an active ingredient, and provides volatilization of a maximum amount of the active ingredient and thus a maximum extent of vermin or insect damage prevention at a minimum amount of input energy.

The present invention provides volatilizing a plenty amount of an active ingredient by using an active ingredient impregnated body or mass that is large in effective area and also by efficient utilization of a wind created.

The present invention is advantageous from the standpoints of either or both of retention and volatilization of an active ingredient.

The present invention provides reliably bringing about vermin or insect damage preventing effect to a maximum possible extent at a minimum of input energy.

An explanation is next given in respect of a third form of embodiment of the present invention.

Figure 5:
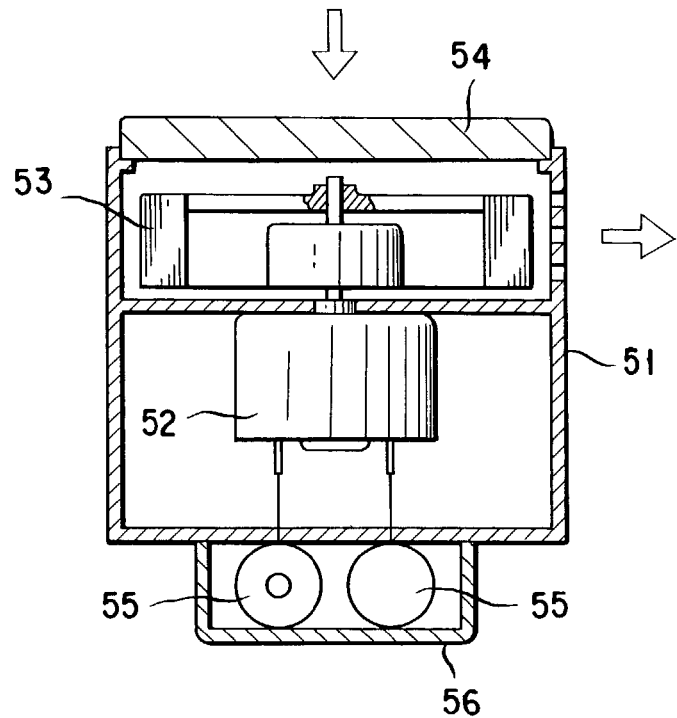
FIG. 5 is a diagrammatic explanatory view of a fan type debugging apparatus for repelling and exterminating noxious or harmful insects according to a third form of the present invention.

Referring to FIG. 5, a fan type debugging apparatus for repelling and exterminating noxious or harmful insects according to the third form of embodiment is provided that comprises a body portion 51 provided with a motor 52, a fan 53 for driving by the motor 52, an active ingredient impregnated body or mass 14 to be ventilated by the fan 53, and a battery 55 that serves as a power supply for the motor 52, wherein the battery, the motor and the fan constitutes a fan type blower for ventilating the active ingredient impregnated body or mass to volatilize an inactive ingredient therein.

The battery 55 is exchangeable by taking off a cover 56.

Such a fan type debugging apparatus was implemented by using a multi-blade fan for the fan 53, a motor having a voltage application of 3.0 volts and a current consumption of 6 milli-amperes (made by Mabuchi Motor Co., Ltd. product RF-330TK) for the motor 52, two unit 3 type alkaline dry cells in series for the battery 55, a particulate cellulose or a mass of cellulose particles for the active ingredient carrier body or mass 54, and terallethrin in an amount of 300 mg for the active ingredient for impregnation in the carrier mass 54.

For experimentation, a fan type debugging apparatus so implemented was placed in a 8 straw mat size (size 13.2 m²) living room and used every day with a running time duration of 12 hours/day.

As a result, the 45-th day the fan blower ran no longer, meaning that it had run for a real total of 480 hours, and in that period of running of the fan blower there had been detected no mosquito bite.

The active ingredient carrier body or mass should preferably be configured in at least one form selected from the group which consists of a form of granules or particles, a form of lines or strips and a form of strings, filament or threads which all provide a large effective area. It should preferably be composed of at least one material selected from the group which consists of cellulose, polymeric water absorptive material, polymeric oil absorptive material and gel. Those selections are desirable from the standpoint of either or both of retention and release of an active ingredient.

For the active ingredient, preference is given of an insecticide or growth control agent which is not only efficacious to a noxious or harmful insect but is high in safety to men and beasts. Such insecticides are preferably pyrethroid insecticides of which terallethrin prallethrin, furamethrin, allethrin and empenthrin are particularly advantageous. Such particular pyrethroid insecticides may be used singly or in combination.

For growth control (inhibiting) agents, at least one chemical may be used as preferred which is selected from the group consisting of pyriproxyfen, methoprene and hydroprene.

Also, compounding an anti-oxidizing agent and/or an ultraviolet absorbing agent into the active ingredient impregnated body and/or compounding an ultraviolet absorbing agent into a casing for the active ingredient impregnated body will enable an implementation of the present invention to be used stably for a prolonged period of time. It also enables use in the outdoors.

End point marking methods which are essential to the preparation of a chemical include a method of using a lipophilic anthraquinone dye for the impregnated body if hydrophilic and utilizing the phenomena that the color of the dye if dissolved in the chemical is recognizable and that when the chemical is evaporated out the dye gets into the body to make its color unrecognizable. Also included is a method of utilizing a color changeable pigment made of a color changeable electron releasing organic compound and a desensitizer, or a color changeable electron releasing organic compound, a desensitizer and a color developer. Further included is a method in which the rate of sublimation of a subliming agent is made substantially equal to the rate of volatilization of the chemical. While any one of these methods may be used singly, the use of a change in color and a subliming agent in combination will make one feel the use actually and thus would be preferred.

The rate of sublimation can be adjusted at a value as required by adjusting the area of a vent opening that may be provided for a casing containing the subliming agent.

Also for the active ingredients described, there is no limitation imposed in using the insecticides and/or rejectants (insect repellents) listed below, in any combination with a proportion as desired.

For example, in killing insects, any one or more of a variety of volatile insecticides so far used may be utilized. Illustrative are pyrethroid insecticides, carbamate insecticides and organophosphorus insecticides. Pyrethroid insecticides are known to be high in safety and have been used well. Specific examples of the pyrethroid insecticides, the organophosphorus insecticides the oxadiazol insecticides and chloro nicotine insecticides have been listed hereinbefore in connection with the first form of embodiment of the present invention. Also, specific examples of growth control agent, specific examples of the repellent and its components, and specific examples of natural volatile oil and its components have been listed hereinbefore in connection with the second form of embodiment of the present invention.

In addition to an anti-oxidizing agent and an ultraviolet absorbing agent for preventing degradation of the active ingredient described, there may be incorporated an inhibitor, depressor and/or retardant for adjusting the amount of volatilization of the active ingredient, a substance or substances having a function or functions of giving out fragrance, deodorizing and/or sterilizing as desired in accordance with the present invention.

For the fan 53 in the fan type blower for use in the present invention, use may be, if air is to flow from the axial direction to the radial direction, be made of a centrifugal fan in which a centrifugal force is applied to impart an energy to the flow. If air is to flow in the axial direction, use may be made of an axial fan in which a lift force of the blade is used to impart energy to the flow.

Illustrative of the centrifugal fan are, for example, a turbo fan, an airfoil fan, a limited load fan, a radial fan, a multi-blade fan and so on.

Here, preferred are centrifugal funs and more preferred is a multi-blade fan.

It is also preferable that a centrifugal fan as mentioned above be placed in a volute, spiral or scroll casing designed to bring together efficiently winds produced by rotating the fan and then to let them out.

In designing the fan type blower made by the fan 53 mounted to the motor 52, it has been found it important that as the load which acts on the motor 52 the index of air resistance f of the fan be taken into account which is equal to motor current consumption $I_1$ with a motor loaded with the fan divided by motor current consumption $I_0$ with the motor unloaded, and that the relationship be made here: $1<f<17$, preferably $1<f<5$.

The index of air resistance f represents the air resistance that a fan blade receives when the fan 53 rotates and is conveniently expressed here by the ratio of current consumption of the motor 52 when it is loaded with the fan 53 to current consumption of the motor 52 when it is unloaded.

As the index of air resistance f increases, the current consumption of the motor 52 loaded with the fan 53 increases. Thus, it has been found that increasing the index of air resistance f to 18 or more significantly reduces the hours in which the fan 53 can run without changing the battery.

Also, increasing the index of air resistance f tends to increase the fan in size. And, increasing the index of air resistance f to 18 or more makes the apparatus body 51 excessively bulky and makes it inconvenient for use. For example, the apparatus will become unhandy.

The fan 53 in size should advantageously have a diameter of 20 to 100 mm, preferably 30 to 60 mm. With a diameter of 20 mm or less, the fan will be too small in diameter to efficiently send air. If it is of axial type, the fan with a diameter of 20 mm or less will have an area of a blade that is too small to give it enough lift force. Also, if it is of centrifugal type, the fan with a diameter of 20 mm or less will be too small in fan diameter to be given enough centrifugal force.

Attempting to obtain enough air flow requires the fan to be rotated with an increased number of rotation. This increases motor current consumption and also requires a higher voltage to be applied. It leads to increasing the number of cells for use and makes the apparatus unsuitable in both total weight and cost.

With a diameter of 100 mm or more, the apparatus 51 will become excessive bulky to the extent that it can no longer be a potable or handy debugging apparatus.

The fan 53 in weight should advantageously range between 1.5 and 8 g. With a weight of less than 1.5 g, the fan 53 will be unable to send air in a necessary and sufficient volume.

With a weight in excess of 8 g, the fan 53 will become too heavy, bringing about the inconveniences that the motor 52 needs for too high a power for starting and must have an excessive current consumption.

The motor 52 as mentioned before should advantageously be a motor of energy saving type that has a voltage application of 3 volts and that can be driven with a current consumption of 35 mA or less when it is unloaded.

The motor 52 having a current consumption of 36 mA or more when it is unloaded significantly reduces the hours in which the fan type blower can run without changing the battery.

For the battery 55, use may be made of one or more of general purpose cells commercially available, such as alkaline dry cells, manganese dry cells and so forth. As illustrative for practical applications of the invention are one unit 3 type manganese dry cell (with a cell capacity of 1200 mA·hr), one unit 3 type alkaline dry cell (with a battery capacity of 2300 mA·hr), two unit 3 type alkaline dry cells (with a battery capacity of 4600 mA·hr), one unit 2 type alkaline cry cell (with battery capacity of 6900 mA·hr), one unit 1 type alkaline dry cell (with a battery capacity of 11500 mA·hr), two unit 2 type alkaline dry cells (with a battery capacity of 13800 mA·hr) and two unit 1 type alkaline dry cells (with a battery capacity of 23000 mA·hr).

The battery capacity here represents a load (amount of current) which makes the "battery life" 1 hour under the assumption that the battery life is the time elapsed for a 1.5 volt battery (cell or cells) in voltage to drop to 0.9 volt. In other words, the battery capacity means the amount of electric current that makes the voltage of a 1.5 volt battery (cell or cells) drop to 0.9 volt in an hour.

While there are slight differences in indicating the battery capacity, there do not affect the present invention, and the battery capacities shown above are illustrative only and are not intended to limit the present invention.

Pre-establishing the index of air resistance f of the fan 53, the size of the fan 53, the weight of fan 53 and the current consumption $I_0$ of the motor 52 when it is unloaded each in the range described provides a debugging apparatus that is portable or handy. These parameters may be so pre-established in various combinations to give rise to such an apparatus with a varied time duration in which they can operate without changing the battery.

Such a time duration, i.e., the hours in which a debugging apparatus as described can operate without changing the battery can be prolonged in accordance with the present invention by establishing the current consumption of the motor loaded with the fan so that the ratio of the operable time duration to the battery capacity has a value of not less than 5%, preferably not less than 10%, and more preferably not less than 20%.

For example, if the fan loaded motor current consumption is set at about 27.4 mA, the apparatus with a battery capacity of about 2300 mA·hr can operate only for a total time duration of about 84 hours, making the ratio of the operable time duration to the battery capacity about 3.7%.

However, if the fan loaded motor current consumption is set at about 20 mA, the apparatus with the same battery capacity can operate for a total time duration of 115 hours, thus making the ratio 5%.

Assuming that the apparatus is used for 12 hours a day, it can be seen that the former with the ratio of 3.7% allows it to be used for 7 days only and the latter with the ratio of 5% permits it to be used for 9 days.

Mention is next made of specific examples of the third form of embodiment of the present invention.

With the use of various types of the fan and motor in an apparatus as shown in FIG. 5, the time duration of the apparatus until it becomes inoperative was measure, however, without using the active ingredient impregnated body or mass 54. The test results are shown in Table 3 below.

TABLE 3

| Test No. | $I_0$ mA | f | $I_1$ mA | 1200 Fan OPT hr | 2300 Fan OPT hr | 4600 Fan OPT hr | 6900 Fan OPT hr | 11500 Fan OPT hr | 13800 Fan OPT hr | 2300 Fan OPT hr | Ratio (%) | Motor used |
|---|---|---|---|---|---|---|---|---|---|---|---|---|
| 1 | 2 | 2 | 4 | 480 | 980 | 1920 | 2880 | 4800 | 5760 | 9600 | 41.7 | Trial product |
| 2 | 2 | 16 | 32 | 60 | 120 | 240 | 360 | 600 | 720 | 1200 | 5.2 | Trial product |
| 3 | 6 | 2 | 12 | 160 | 320 | 640 | 980 | 1600 | 1920 | 3200 | 13.9 | Mabuchi Motor Co., Ltd. RF-330TK |
| 4 | 6 | 5 | 30 | 64 | 128 | 256 | 384 | 640 | 768 | 1280 | 5.6 | Mabuchi Motor Co., Ltd. RF-330TK |
| 5 | 14 | 2 | 28 | 69 | 137 | 274 | 411 | 686 | 823 | 1371 | 6.0 | Matsushita Electric Works, Ltd. MDN3BT3CPA |
| 6 | 22 | 1.5 | 33 | 58 | 116 | 233 | 349 | 582 | 698 | 1164 | 5.1 | Tokyo Parts Industry, Ltd. FC8 |
| 7 | 30 | 1.1 | 33 | 58 | 116 | 233 | 349 | 582 | 698 | 1164 | 5.1 | Tokyo Parts Industry, Ltd. FSB3 |
| Com. 1 | 2 | 20 | 40 | 48 | 96 | 192 | 288 | 480 | 576 | 980 | 4.2 | Trial product |
| Com. 2 | 6 | 18 | 10 | 18 | 36 | 71 | 107 | 178 | 213 | 356 | 1.5 | Mabuchi Motor Co., Ltd. RF-330TK |
| Com. 3 | 14 | 2.3 | 32.2 | 45 | 90 | 180 | 270 | 450 | 540 | 900 | 3.9 | Matsushita Electric Works, Ltd. MDN3BT3CPA |
| Com. 4 | 22 | 5 | 110 | 17 | 35 | 70 | 105 | 175 | 209 | 349 | 1.5 | Tokyo Parts Industry, Ltd. FC8 |
| Com. 5 | 40 | 2 | 80 | 24 | 48 | 96 | 144 | 240 | 288 | 480 | 2.1 | Tokyo Parts Industry, Ltd. FSB3 |
| Com. 6 | 50 | 20 | 10.00 | 2 | 4 | 8 | 12 | 19 | 23 | 38 | 0.2 | Mabuchi Motor Co., Ltd. RE-140RA |

$I_0$: Current Consumption of the motor unloaded.
$I_1$: Current consumption of the motor loaded with the fan
f: Index of fan air resistance
Fan OPT (hr: Fan operating hours)
Ratio: Fan OPT hr/Battery capacity (mA · hr) (%)
Com: Comparative test Current consumption was measured using Kenwood Co., Digital Multimeter DL-712. Measurement was made at a wiring between the motor 52 and the battery 55.

Test Nos. 1 to 7 met all of the three requirements described of this form of embodiment of the invention.

Comparative Tests 1 to 6 include those which met only one of the three requirements of the invention, those which met two of those requirements and those which met all of those requirements.

Compare test results of Test Nos. 1 and 2 with those of Comparative Test 1. All these tests used the same motor. Comparing Test No. 1 with Comparative Test 1, it is seen that between those tests using the same battery capacity of 2300 mA·hr (corresponding to two unit 3 type alkaline cells connected in series) there is a difference in fan operating time as many as 24 hours. And, if the battery capacity is raised to 23000 mA·hr (corresponding to two unit 1 type alkaline cells connected in parallel), the difference in fan operating time duration becomes as many as 220 hours, thus manifesting a significant economical difference. Comparison of Test No. 1 with Comparative Test 1 manifests even more the economical difference between the inventive apparatus and the prior art.

Comparison of Test Nos. 3 and 4 with Comparative Test 2 has the same or similar results.

Next, compare test results of Test No. 5 with those of Comparative Test 3. Comparative Test 3 used a current consumption of the motor unloaded and an index of air resistance of the fan each within the corresponding requirement of the present invention but, having the result of a poor operating time duration, represents an example showing that economy is not attainable depending on a certain combination of them. Using a battery capacity of 2300 mA·hr (corresponding to two unit 3 type alkaline cells connected in series), it is seen that Test No. 5 had a fan operating time duration longer than Comparative Test 3 by as many as 47 hours. And, if the battery capacity is raised to 23000 mA·hr (corresponding two unit 1 type alkaline cells connected in parallel), the difference in fan operating time duration becomes as many as 471 hours.

Comparison of Test No. 6 with Comparative Test 4 has the same or similar results.

Next, compare the test results of Test No. 3 with those of Comparative Test 5. These tests used the same fan index of air resistance (not meaning that they used the same fan). Comparative Test 5 had a current consumption of the motor unloaded that is outside of the range the present invention requires. Comparison of these tests makes the difference manifest.

It should be noted that Comparative Test 6 which satisfied none of the requirements evidences uneconomicalness of the prior art.

From the foregoing test results, it will be evident that satisfying all of the requirements according to the present form of embodiment of the invention provides a prolonged fan operating time duration.

A fan type debugging apparatus according to this form of the present invention allows a motor to be driven and thus a fan to send air to and ventilate a body or mass impregnated with an active ingredient, over a prolonged total number of hours without changing the battery, thereby permitting the active ingredient to volatilize over such an extended time period without requiring a battery change.

There is also provided a portable or handy debugging apparatus for repelling and exterminating noxious or harmful insects.

An explanation is next given in respect of a fourth form of embodiment of the present invention.

Figure 6:
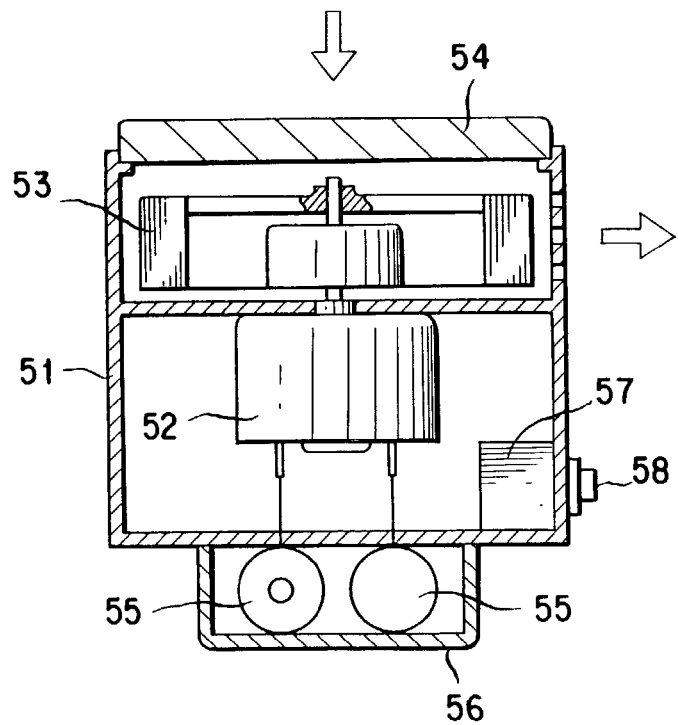
FIG. 6 is a diagrammatic explanatory view of a fan type debugging apparatus for repelling and exterminating noxious or harmful insects according to a fourth form of the present invention.

Referring to FIG. 6, an apparatus according to the forth form of embodiment of the invention comprises an apparatus body or body portion 51 provided with an electric motor 52, a fan 53, a body or mass 54 impregnated with an active ingredient and a battery 55. The battery 55 can be replaced for by putting a cover 56 out of place.

The motor 52 and the fan 53 constitute a fan type blower which sends air to and ventilates the active ingredient impregnated body or mass 54 to volatilize the active ingredient.

The apparatus body portion 51 also incorporates a current control circuit unit 57 such as a timer that controls power to the motor 52. By manipulating an operating member 58 such as a dial provided therefor, the power control circuit unit 57 is designed to turn the energizing current to the motor 52 on and off alternately.

Figure 7:
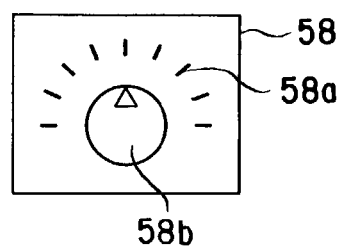
FIG. 7 is a front view of an operating member in the apparatus shown in FIG. 6.
Figure 8:
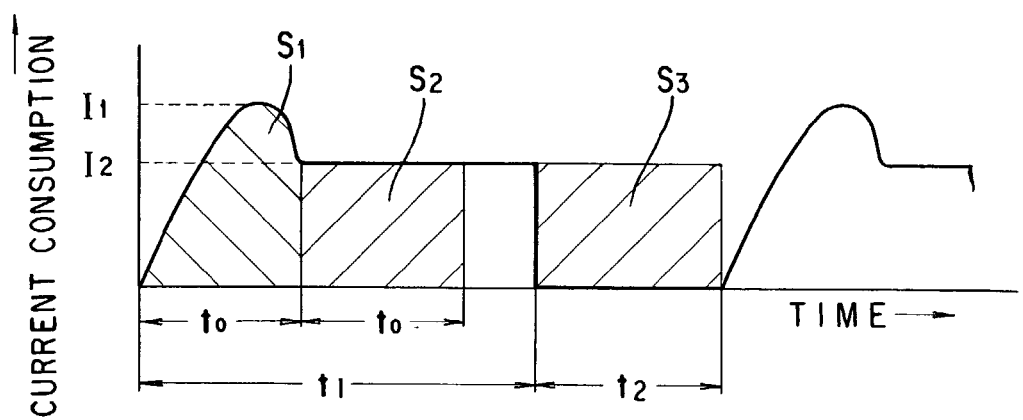
FIG. 8 is an explanatory diagram that illustrates the amount of electric current consumed in the apparatus shown in FIG. 6 while it is cyclically turned on and off.

For example, the operating member 58 as shown in FIG. 7 may have graduations 58a and a knob or button 58b such that setting the button 58b to a given graduation 58a establishes a particular current on and off time as desired.

The current control circuit unit 57 may have an operating and a halting time period pre-established therein so that with a power switch turned on, the motor 52 may be driven for the pre-established operating time period and may be halted for the pre-established halting time period with the cycle repeated.

The operating and halting time periods have the following relationship.

The halting time period is here defined as a time period that in the length of time is not greater than 9 (nine) times as long as the operating time period and in which the amount of electric current (quantity of electricity) not lost is greater than the amount of electric current (quantity of electricity) which is consumed when the motor commences to be driven and which is in excess of a stable electric current that appears thereafter.

Mention is made more specifically of the halting time period.

The electric current rises to a value $I_1$ when the motor commences to be driven. A lower stable value of electric current $I_2$ appears with a certain lapse of time $t_0$ after the current begins to flow.

The amount of electric current (quantity of electricity) $S_1$ that is consumed after the motor starts to be driven and within the lapse of time $t_0$ until the current becomes stable is greater than the amount of electric current (quantity of electricity) $S_2$ that is consumed within the same length of time $t_0$ after the current becomes stable. And, there is an excess current consumption (consumed quantity of electricity): $S_1 - S_2$.

If the motor is driven or operated for a time period $t_1$ and halted for a time period $t_2$, then the amount of electric current (quantity of electricity) $S_3$ not consumed during the halting time period $t_2$ is expressed by $t_2 \times I_2$ (stable electric current magnitude).

If the amount of electric current (quantity of electricity) $S_3$ that is not consumed in the halting time period $t_3$ is less than the excess current consumption (consumed quantity of electricity) $S_1 - S_2$ that occurs when the motor starts to be driven, then it does not make sense to apply an electric current intermittently because the total current consumption (consumed quantity of electricity) when the current is applied intermittently becomes greater than the total current consumption (consumed quantity of electricity) when the current is applied continuously. Accordingly, the halting time period $t_2$ must be a time period as mentioned above in which the amount of electric current (quantity of electricity) $S_3$ not consumed in the time period $t_2$ is greater than the excess current consumption (consumed quantity of electricity): $S_1-S_2$ when the motor starts to be driven.

Such a halting time period $t_2$ is expressed by the inequity: $t_2>(S_1-S_2)/I_2$.

The operating time period and the halting time period can be pre-established, depending on purposes, in various manners, e.g., in units of days, hours, minutes and seconds. For example, the motor (fan) may periodically be operated or driven for one day and halted for one day, driven for 1 hour and halted for 2 hours, driven for 10 minutes and halted for 50 minutes, and/or operated for 30 seconds and halted for 20 seconds.

A halting time period of any length of time is sufficient unless it is less than 9 times as long as the operating or driving time period. It should, of course, be established with due consideration taken for room active ingredient richness at the halting time period, and a reduction in room active ingredient richness per unit of time.

Also, the operating time period must be a time period that is efficacious and enough to exterminate a particular noxious or harmful insect or insects to be exterminated. For example, for female stegomyia mosquitoes it is a time period required for their 50% to be knocked down or for them to refrain from taking bloodsucking behavior. For clothes moths it is a time period needed for their 50% to be knocked down or for them to refrain from taking food harming behavior. The operating time period is determined with a combination of a particular noxious or harmful insect, a particular active ingredient and a particular motor taken into account.

For the fan in the fan type blower for use in the present invention, use may, if air is to flow from the axial direction to the radial direction, be made of a centrifugal fan in which a centrifugal force is applied to impart an energy to the flow. If air is to flow in the axial direction, use may be made of an axial fan in which a lift force of the blade is used to impart energy to the flow.

Illustrative of the centrifugal fan are, for example, a turbo fan, an airfoil fan, a limited load fan, a radial fan, a multi-blade fan and so on.

Here, preferred are centrifugal funs and more preferred is a multi-blade fan.

It is also preferable that a centrifugal fan as mentioned above be placed in a volute, spiral or scroll casing designed to bring together efficiently winds produced by rotating the fan and then to let them out.

Also, illustrative for the battery or cell used to power driving the fan type blower are, for example, a primary cell or battery such as an alkaline dry cell, a manganese dry cell, a button type cell, an air cell or lithium ion cell, and a secondary cell or battery such as a nickel cadmium battery or a lithium ion cell.

A suitable choice of a particular cell or battery may be made in conjunction with its kind (e.g., either alkaline or manganese, or unit 1 or unit 2 type), its number and its manner of connection (parallel or series) in consideration of its use conditions and period, the kind of the motor and fan used.

The active ingredient impregnated body should preferably have a shape or configuration which besides a honeycomb form having an air or gas rectifying function is a form of material that is large in effective area which is at least one material selected from the group that consists of a mass of granules, a mass of strips and a mass of strings, filaments or threads. It is also preferable from the standpoints of retention and/or release of the active ingredient that the particulate material forming the active ingredient impregnated body be composed of at least one material selected from the group which consists of a cellulose, a polymeric water absorptive agent, a polymeric oil absorptive agent and a gel.

The active ingredient is preferably an insecticide or a growth control agent that is effective to one or more kinds of insecticides but is not harm to men and beasts.

The insecticides should preferably be pyrethroid insecticides of which at least one chemical selected from the group which consists of terallethrin, prallethrin, furamethrin, allethrin, and empenthrin is particularly advantageous.

For growth control (inhibiting) agents, at least one chemical is preferred which is selected from the group consisting of pyriproxyfen, methoprene and hydroprene.

Also, compounding an anti-oxidizing agent and/or an ultraviolet absorbing agent into the active ingredient impregnated body and/or compounding an ultraviolet absorbing agent into a casing for the active ingredient impregnated body will enable an implementation of the present invention to be used stably for a prolonged period of time. It also enables use in the outdoors.

End point marking methods which are essential to the preparation of a chemical include a method of using a lipophilic anthraquinone dye for the impregnated body if hydrophilic and utilizing the phenomena that the color of the dye if dissolved in the chemical is recognizable and that when the chemical is evaporated out the dye gets into the body to make its color unrecognizable. Also included is a method of utilizing a color changeable pigment made of a color changeable electron releasing organic compound and a desensitizer, or a color changeable electron releasing organic compound, a desensitizer and a color developer. Further included is a method in which the rate of sublimation of a subliming agent is made substantially equal to the rate of volatilization of the chemical. While any one of these methods may be used singly, the use of a change in color and a subliming agent in combination will make one feel the use actually and thus would be preferred.

The rate of sublimation can be adjusted at a value as required by adjusting the area of a vent opening that may be provided for a casing containing the subliming agent.

Also for the active ingredients described, there is no limitation imposed in using the insecticides and/or rejectants (insect repellents) listed below, in any combination with a proportion as desired.

For example, in killing insects, any one or more of a variety of volatile insecticides so far used may be utilized. Illustrative are pyrethroid insecticides, carbamate insecticides and organophosphorus insecticides. Pyrethroid insecticides are known to be high in safety and have been used well. Specific examples of the pyrethroid insecticides, the organophosphorus insecticides the oxadiazol insecticides and chloro nicotine insecticides have been listed hereinbefore in connection with the first form of embodiment of the present invention. Also, specific examples of growth control agent, specific examples of the repellent and its components, and specific examples of natural volatile oil and its components have been listed hereinbefore in connection with the second form of embodiment of the present invention.

In addition to an anti-oxidizing agent and an ultraviolet absorbing agent for preventing degradation of the active ingredient described, there may be incorporated an inhibitor, depressor and/or retardant for adjusting the amount of volatilization of the active ingredient, a substance or substances having a function or functions of giving out fragrance, deodorizing and/or sterilizing as desired in accordance with the present invention.

Mention is next made of tests and their results.

Using a fan type debugging apparatus as shown in FIG. 6, tests were conducted as for bloodsucking by female stegomyia mosquitoes.

The motor used in the fan type debugging apparatus was an motor of model RF-330TK made by Mabuchi Motor Co., Ltd.

The battery consisted of two unit 3 type alkaline cells connected in series.

The chemical used was terallethrin and the impregnatable or carrier body was a mass of granules or particles made of a cellulose.

Conditions of the tests were as follows:

The tests were carried out in 4.5, 8, 10 and 12 straw mat (7.4, 13.2, 16.5 and 19.8 $m^2$) living rooms.

One of the four walls of each room had a ventilating window of 1 m×1 m size which was left open in all the times.

A room temperature of 25° C. was held substantially constant.

The period of each of the tests was for half a year (180 days).

Ones of which use periods are less than half a year was replaced each time.

The days of measurement were 1st, $15^{th}$, $30^{th}$, $60^{th}$, and $120^{th}$ days.

In each of the rooms an air permeable cage was placed in which one (1) female mouse was loosed together with twenty (20) female stegomyia mosquitoes and its bloodsucking was checked after 24 hours.

The amount of charge of the chemical was set up for each number of straw mats (area).

The test results were marked with ⊚ if the rate of knock-down is 90% or more, with ○ if it is 50% or more and with Δ if it is less than 50%, and with X if there was bloodsucking.

The results of the test in the 4.5 straw mat (7.4 $m^2$) room are shown in Table 4 below.

TABLE 4

Results of Tests in a 4.5 Straw Mat Room

| Test No. | Amount of Charge | $t_2/t_1$ | Days of Use | 1-st Day | 15-th Day | 30-th Day | 60-th Day | 120-th Day |
|---|---|---|---|---|---|---|---|---|
| Test 1 | 1.3 g | 2 | 60 days | ⊚ | ⊚ | ⊚ | ○ | ○ |
| Test 2 | 1.3 g | 5 | 120 days | ⊚ | ○ | ○ | ○ | ○ |
| Test 3 | 1.3 g | 9 | 200 days | ○ | Δ | Δ | Δ | Δ |
| Com. Test 1 | 1.3 g | Continuous | 20 days | ⊚ | ○ | ⊚ | ⊚ | ○ |
| Com. Test 2 | 1.3 g | 10 | 220 days | Δ | x | Δ | x | x |
| Com. Test 3 | 1.3 g | $t_2 < (S_1 - S_2)/I_2$ | 18 days | ⊚ | ○ | ⊚ | ⊚ | ○ |

The results of the test in the 8 straw mat (13.2 $m^2$) room are shown in Table 5 below.

TABLE 5

Results of Tests in a 8 Straw Mat Room

| Test No. | Amount of Charge | $t_2/t_1$ | Days of Use | 1-st Day | 15-th Day | 30-th Day | 60-th Day | 120-th Day |
|---|---|---|---|---|---|---|---|---|
| Test 1 | 2.2 g | 2 | 60 days | ⊚ | ⊚ | ○ | ⊚ | ○ |
| Test 2 | 2.2 g | 5 | 120 days | ⊚ | ⊚ | ○ | ○ | Δ |
| Test 3 | 2.2 g | 9 | 200 days | ○ | Δ | Δ | Δ | Δ |
| Com. Test 1 | 2.2 g | Continuous | 20 days | ⊚ | ○ | ⊚ | ⊚ | ○ |
| Com. Test 2 | 2.2 g | 10 | 220 days | Δ | x | x | x | x |
| Com. Test 3 | 2.2 g | $t_2 < (S_1 - S_2)/I_2$ | 18 days | ⊚ | ○ | ⊚ | ⊚ | ○ |

The results of the test in the 10 straw mat (16.5 $m^2$) room are shown in Table 6 below.

TABLE 6

Results of Tests in a 10 Straw Mat Room

| Test No. | Amount of Charge | $t_2/t_1$ | Days of Use | 1-st Day | 15-th Day | 30-th Day | 60-th Day | 120-th Day |
|---|---|---|---|---|---|---|---|---|
| Test 1 | 2.8 g | 2 | 60 days | ⊚ | ⊚ | ○ | ⊚ | ○ |
| Test 2 | 2.8 g | 5 | 120 days | ⊚ | ⊚ | ○ | ○ | Δ |
| Test 3 | 2.8 g | 9 | 200 days | ○ | Δ | Δ | Δ | Δ |
| Com. Test 1 | 2.8 g | Continuous | 20 days | ⊚ | ○ | ⊚ | ⊚ | ○ |
| Com. Test 2 | 2.8 g | 10 | 220 days | Δ | x | x | x | x |
| Com. Test 3 | 2.8 g | $t_2 < (S_1 - S_2)/I_2$ | 18 days | ⊚ | ○ | ⊚ | ⊚ | ○ |

The results of the test in the 12 straw mat (19.8 m$^2$) room are shown in Table 7 below.

TABLE 7

Results of Tests in a 12 Straw Mat Room

| Test No. | Amount of Charge | $t_2/t_1$ | Days of Use | 1-st Day | 15-st Day | 30-st Day | 60-st Day | 120-st Day |
|---|---|---|---|---|---|---|---|---|
| Test 1 | 3.3 g | 2 | 60 days | ⊚ | ⊚ | ⊚ | ○ | ○ |
| Test 2 | 3.3 g | 5 | 120 days | ⊚ | ○ | ○ | ○ | Δ |
| Test 3 | 3.3 g | 9 | 200 days | ○ | Δ | Δ | Δ | Δ |
| Com. Test 1 | 3.3 g | Continuous | 20 days | ⊚ | ○ | ⊚ | ⊚ | ○ |
| Com. Test 2 | 3.3 g | 10 | 220 days | Δ | Δ | x | x | x |
| Com. Test 3 | 3.3 g | $t_2 < (S_1 - S_2)/I_2$ | 18 days | ⊚ | ○ | ⊚ | ⊚ | ○ |

Test Nos. 1 to 3 were longer in days of use than Comparative Test 1 in which electric current is applied continuously, but were able to achieve efficacy equivalent to that achieved by Comparative Test 1. Test No. 1 allowed days of use three times longer than the case of continuous use but had the efficacy substantially equal to that achievable by the latter. Test No. 2 allowed days of use six times longer than the case of continuous use and had no bloodsucking although it saw some drop in efficacy towards the end of the days. Test No. 3 failed to achieve an eminent knock-down, but were so efficacious enough to prevent blood sucking and allowed days of use 10 times longer than the case of continuous use.

Comparative Test 2 was long in days of use but had bloodsucking by mosquitoes.

Comparative Test 3 was enough in efficacy, but became short in days of use in spite of the fact that current is turned on and off, evidently because of the failure to satisfy the requirement: $t_2 > (S_1 - S_2)/I_2$.

It has thus been shown that a fan type debugging apparatus according to the present invention if used in a living space achieves sufficient efficacy and maintains the same for a prolonged period of time.

It will be appreciated that any of the second to fourth forms of embodiment of the present invention as described is applicable individually in a combination to the first form of embodiment of the invention described.

An explanation is next given in respect of a fifth form of embodiment of the present invention.

In order to resolve Problem (1) mentioned hereinbefore in the discussion of the Background Art, a chemical impregnated or carrier body (an active ingredient impregnated or carrier body) is made granular or particulate, i.e., made in the form of a mass of particles or granules, and these chemical impregnated or carrier particles or granules are themselves agitated. This has been found to make even the amounts of wind or air flows which the carriers receive, thereby preventing the amount of the chemical that remained in the chemical impregnated particulate mass or body from varying depending on a local site in air flow direction. The effects have been demonstrated from the tests conducted of which methods and test results are stated below.

A test apparatus was made on placing in a square wind blow outlet of 8 cm side an impregnated body receptacle made of a cylinder of 8 cm inner diameter and 10 cm height and with nets put up to cover its top and bottom. The receptacle accommodated therein a mass of 2 grams in weight of granules having a diameter of 4 mm and impregnated with a chemical of 300 milligrams in weight. Local variations were measured of the amount of the chemical that remained in that mass after a run of three (3) full (24 hours) days.

As a comparative, local variation were also measured of the chemical that remained in a monolithic immobile body of honeycomb shape impregnated with the chemical placed in a same square wind blow outlet of 8 cm side. Test results are shown in Table 8 below.

TABLE 8

| Site* of Measurement | Granular Mass impregnated with Chemical (Invention) | Monolithic Body Impregnated with Chemical (Comparative) |
|---|---|---|
| 0~1 cm | 63.81 | 41.02 |
| 2~3 cm | 65.30 | 73.24 |
| 4–5 cm | 64.97 | 95.67 |

Numeric values in the table indicate amounts that remain for 100 of charge of the chemical. Each site of measurement is indicated by the distance from the blow outlet of the chemical impregnated mass or body.

In Table 8, the numeric values each indicate an amount that remains for 100 of charge of the chemical. Each site of measurement is indicated by the distance from the blow outlet of the chemical impregnated granular mass or monolithic body.

When use is made of a chemical impregnated monolithic body, it is seen that a chemical tends to volatilize more at sites closer to the fan blow outlet, and very little at sites remote from it where 90% or more of the chemical tends to remain. In contrast, if use is made of a granular or particulate mass impregnated with the chemical, it is shown that there is substantially no difference in the amount than remains between locally different sites by virtue of the fact that the chemical impregnated granular or particulate mass while being constantly agitated acts to volatilize the chemical.

Also, in order to resolve Problem (2) mentioned previously in the discussion of the Background Art, a measure as mentioned below has been taken. Thus, the chemical impregnated body is made in the form of a mass of particles or granules whose number in a given space is increased. This makes smaller each individual chemical carrying particle or granules and in turn makes shorter the distance of travel of the chemical. As a result, the chemical as it volatilizes from the outer surfaces of the chemical impregnated particulate mass is more quickly replenished from the interior into those outer surfaces, thereby making the density or concentration of the chemical in the mass even over its entire volume. A state of stabilized volatilization of the chemical is thus established. Further, it is also conceivable to add any of various kinds of solvents as a measure to promote evenness in distribution of the chemical on each individual chemical carrying particle or granule. This is found to be an effective measure for a chemical that is high in viscosity and low in mobility.

Tests were also conducted to investigate patterns of volatilization of a chemical from a chemical impregnated particulate mass according to the present invention and a chemical impregnated monolithic body in the prior art. Each of these chemical carriers had an identical kind and amount of chemical impregnated therein, and was run for fifteen (15) consecutive days. On each of the fifth, tenth and fifteenth day a measurement is made of the amount of the chemical that remained, from which the amount of volatilization of the chemical per unit time is estimated. Test results are shown in Table 9 below and also in the graph of FIG. 9.

TABLE 9

| Chemical Carrier | Days of Running | | | Initial Charge Amount (mg) | Amount that remained (mg) | Effective Rate of Volatilization (%) |
|---|---|---|---|---|---|---|
| | 0–5 | 5–10 | 10–15 | | | |
| Chemical Impregnated Particulate Mass | 2.64 | 2.50 | 2.33 | 1005 | 105.93 | 89.46 |
| Chemical Impregnated Monolithic Body | 2.59 | 2.18 | 1.29 | 998 | 273.65 | 72.58 |

Figure 9:
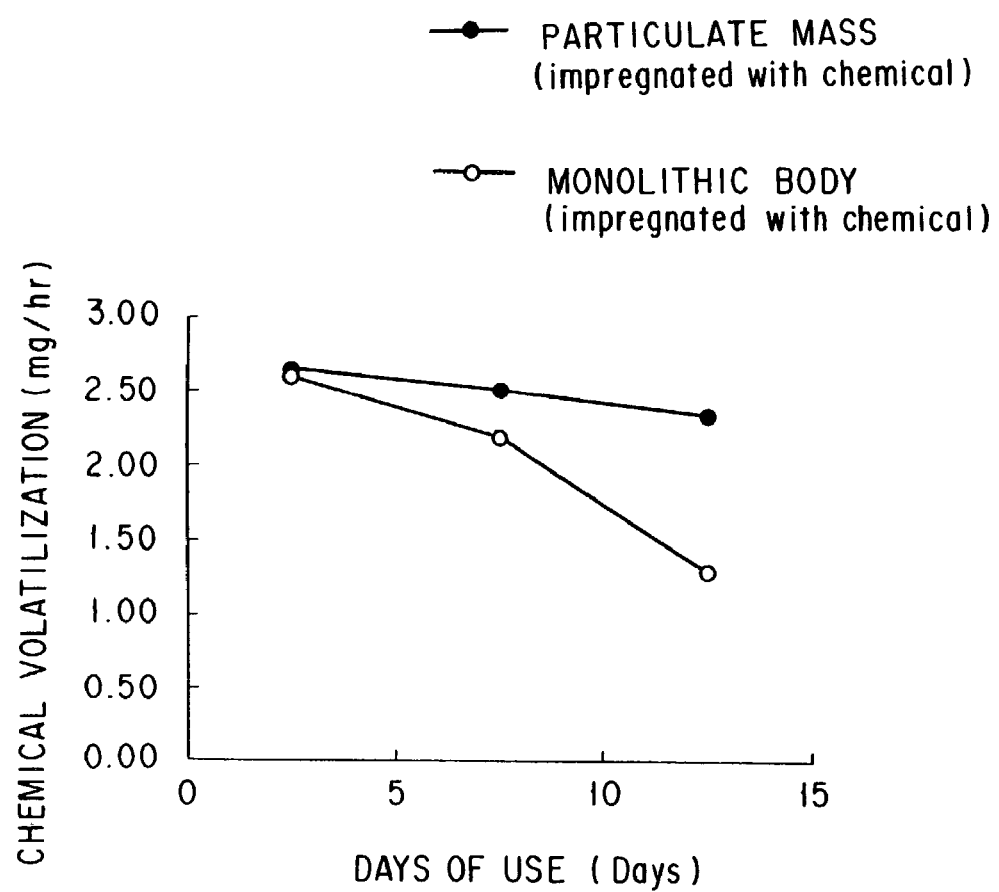
FIG. 9 is a graph in which the rates of chemical volatilization for different types of bodies impregnated with a given chemical are plotted with respect to days of use in a fifth embodiment of the present invention.

From the test results shown in Table 9 above and the graph of FIG. 9, it is seen that in the monolithic body the rate of volatilization is lowered substantially proportionally from the start of running while in the particulate mass the amount of volatilization is stably maintained. This stabilized amount of volatilization over a prolonged time period is thought to be attributable to the fact that agitating or stirring the chemical carrier particles used to form the chemical impregnated mass makes even the concentration of the chemical over its entire volume and causes the chemical to flow or move dynamically on each individual carrier particle. It is also thought to be attributable to the fact that a reduction in weight as a result of volatilization of the chemical causes lowering the specific gravity of each of the mass and the impregnant chemical, which in turn increases the mobility of the chemical carrier particles; as a result, the increased mobility still maintains the amount of volatilization of the chemical substantially at a given level though the concentration of the chemical is lowered.

Also, as for the effective rate of volatilization which is the proportion of the amount of chemical that is its initial charge amount minus the amount that remains on the $15^{th}$ day to its initial charge amount shown in Table 9, it is seen that the value of 89.46% in the case of the particulate mass compared with the value of 72.58 in the case of monolithic body indicates that the particulate mass allows a highly efficient volatilization of the chemical.

Further, in order to resolve Problem (3) mentioned hereinbefore in the discussion of the Background Art, a measure as stated below has been taken. Thus, effective utilization of energy is attained by causing chemical carrier particles as the chemical impregnated mass to receive both types of winds, i.e., winds from the fun and winds created when they are themselves rotated. This makes the total required surface area of the mass as a whole smaller than that of a conventional body, and reduces the loss of a wind force. Table 10 shows results of tests using a chemical impregnated particulate mass according to the present invention and a chemical impregnated monolithic body of honeycomb shape in the prior art in which both the particulate mass and monolithic body had an identical real volume, and a wind force was measured at each of sites 5 cm upper and 10 cm upper, respectively, of the chemical volatilizing outlet. The test results, here again, show that the particulate porous mass is more favorable than the monolithic porous body, by evidencing that the former produces a greater wind speed, and is lesser in the loss of wind force, than the latter.

TABLE 10

| | Wind Speed (m/sec) | | |
|---|---|---|---|
| Site of Measure | Chemical impregnated Particulate Mass | Chemical impregnated Monolithic Body | Chemical impregnated Mass or Body Uninstalled |
| 5 cm upper from volatilizing outlet | 1.6 | 1.0 | 2.4 |
| 10 cm upper from volatilizing outlet | 0.8 | 0.5 | 1.2 |
| Real Volume of chemical impregnated Mass or Body (cm$^3$) | 4.05 | 4.10 | — |

The foregoing tests and test results have also revealed the following: Thus, in order to maintain the amount of volatilization of a chemical over a prolonged time period by preventing local variation of volatilization in the chemical impregnated particulate mass while effectively utilizing wind force energy of the fan, it is desirable that the chemical carrier particles forming the particulate mass be stirred or agitated moderately or to a proper extent. To this end, it has been found that certain requirements as mentioned below be met.

First, there is a requirement that relates to the configuration of the chemical carrier particles. It is desirable that the chemical carrier particles have a shape that minimizes their mutual frictional drag or resistance leading to a loss of energy when they are agitated, i.e., a shape of particles such that the maximum area of contact of one particle with another be not in excess of one half of its total surface area. Specifically, it is desirable that the chemical carrier particles be each in the form of a sphere which should be the shape that provides a minimum friction.

A second requirement for the chemical carrier particles requires that the particles as a particulate mass have an appropriate set of abilities for the chemical, i.e., the ability to be loaded (impregnated) with the chemical, the ability to unload (release) the chemical, and the ability to promote the chemical to be made even quickly in the particulate mass. The ability to be loaded with chemical depends on the real volume of the particulate mass, and the ability to unload the chemical and the ability to promote the chemical to be quickly made even depend on the density and thus the porosity of the particulate mass.

The real volume of a particulate mass required for this aspect of the present invention can be derived from its porosity and apparent volume, and can be adjusted as desired in a range as mentioned below with the properties of the chemical such as its vapor pressure and viscosity taken into account. The real volume of a chemical carrier particulate mass, as expressed by [apparent volume×(1−porosity/100)], should desirably range, for each particle, from $5\times10^{-5}$ to $5\times10^5$ mm$^3$, preferably from $5\times10^{-3}$ to $5\times10^3$ mm$^3$, more preferably from $5\times10^{-2}$ to $5\times10^{-1}$ mm$^3$. And, the amount of volatilization and the number of days in which efficacy is to last can be adjusted by the number of the chemical carrier particles and the concentration of the chemical to be carried thereby.

A third requirement for the chemical carrier or impregnated particulate mass requires that it have a specific gravity in a range from 0.005 to 0.5 when the air flow per unit time of the wind that passes through a receptacle which accommodates the chemical carrier particulate mass ranges between 0.01 and 1.0 m$^3$/min. If, however, a large fan having an air flow of 1.0 m$^3$/min or more is used, the chemical carrier particulate mass can be used even if it has a specific gravity of 0.5 or more.

A fourth requirement may further be included that requires that either or both of the chemical carrier particulate mass or its receptacle be processed for an antistatic. For there is a possibility that an electrostatic if it develops may act to impede agitation between the chemical carrier particles or between the chemical carrier particles and their receptacles.

In view of the foregoing, a chemical volatilizing apparatus is provided in accordance with the present invention, characterized in that a mass of a particulate material or particles is accommodated in a receptacle and is impregnated therein with a chemical to serve as a carrier therefor, the carrier particles being ventilated with winds from a fan and, while being agitated or stirred by wind forces, permitting the chemical impregnated in the particulate mass to volatilize.

A chemical volatilizing apparatus according to the present invention as described is also characterized in that each of the chemical carrier particles should preferably have a shape such that the maximum area of contact of one particle with another is not more than one half of the total surface area of the particle.

A chemical volatilizing apparatus according to the present invention as described is also characterized in that the real volume of a chemical carrier particulate mass, as expressed by [apparent volume×(1−porosity/100)], should desirably range, for each particle, from $5\times10^{-5}$ to $5\times10^5$ mm$^3$, preferably from $5\times10^{-3}$ to $5\times10^3$ mm$^3$, more preferably from $5\times10^{-2}$ to $5\times10^{-1}$ mm$^3$.

A chemical volatilizing apparatus according to the present invention as described is also characterized in that the chemical carrier or impregnated particulate mass should preferably have a specific gravity in a range from 0.005 to 0.5 when the air flow per unit time of the wind that passes through a receptacle which accommodates the chemical carrier particulate mass ranges between 0.01 and 1.0 m$^3$/min.

A chemical volatilizing method according to the present invention as described is further characterized in that either or both of the chemical carrier particulate mass for chemical volatilization or its receptacle should preferably be pre-processed for an antistatic.

While mention is made below of specific examples of this aspect of the present invention, it should be understood that the present invention is not limited thereto.

A chemical for use in the present invention as impregnated in the chemical carrier particulate mass may be any one of known volatile chemicals should be selected according to an aimed use thereof.

For example, in killing insects, any one or more of a variety of volatile insecticides so far used may be utilized. Illustrative are pyrethroid insecticides, carbamate insecticides and organophosphorus insecticides. Pyrethroid insecticides are known to be high in safety and have been used well, of which specific examples are listed below, each given in the order of the general name, the chemical name and the parenthesized trade name followed by the producer.

allethrin: 3-allyl-2-methyl cyclopenta-2-ene-4-one-1-yl dl-cis/trans-chrysanthemat (Pynamin, Sumitomo Chemical Co.)

dl·d-T80-allethrin: 3-allyl-2-methyl cyclopenta-2-ene-4-one-1-yl d-cis/trans-chrysanthemat (Pynamin forte, Sumitomo Chemical Co.)

dl·d-T-allethrin: 3-allyl-2-methyl cyclopenta-2-ene-4-one-1-yl d-trans-chrysanthemat (Bioallethrin)

d·d-T-allethrin: d-3-allyl-2-methyl cyclopenta-2-ene-4-one-1-yl d-trans-chrysanthemat (Esbiol)

d·d-T80-prallethrin: d-2-methyl-4-oxo-3-propargyl cyclopento-2-enyl d-cis/trans-chrysanthemat (Etoc, Sumitomo Chemical Co.)

phthalthrin: N-(3,4,5,6-tetrahydrophthalimide)-methyl d1-cis/trans-chrysanthemat (Neopynamin, Sumitomo Chemical Co.)

d-T80-phthalthrin: (1,3,4,5,6,7-hexahydro-1,3-dioxo-2-indolyl)methyl d-cis/trans-chrysanthemat (Neopynamin forte, Sumitomo Chemical Co.)

resmethrin: 5-benzyl-3-furylmethyl d1-cis/trans-chrysanthemat (Chrythron, Sumitomo Chemical Co.)

d·d-T80-resmethrin: 5-benzyl-3-furylmethyl d-cis/trans-chrysanthemat (Chrythron forte, Sumitomo Chemical Co.)

permethrin: 3-phenoxybenzyl d1-cis/trans-2,2-dimethyl-3-(2,2-dichlorovinyl) cyclopropane carboxylate (Eksmin, Sumitomo Chemical Co.)

phenothrin: 3-phenoxybenzyl d-cis/trans-chrysanthemat (Sumithrin, Sumitomo Chemical Co.)

fenvalerate: α-cyano-3-phenoxybenzyl-2-(4-chlorophenyl)-3-methyl butylate (Sumicidin, Sumitomo Chemical Co.)

cypermethrin: α-cyano-3-phenoxybenzyl d1-cis/trans-3-(2,2-dichlorovinyl)-2,2-dimethyl cyclopropane carboxylate (Agrothrin, Sumitomo Chemical Co.)

cyphenothrin: α-cyano-3-phenoxybenzyl d-cis/trans-chrysanthemat (Gokilaht, Sumitomo Chemical Co.)

empenthrin: 1-ethynyl-2-methyl pento-2-enyl d-cis/trans-chrysanthemat (Vaporthrin, Sumitomo Chemical Co.)

terallethrin: 2-allyl-3-methyl-2-cyclopentene-1-one-4-yl-2,2,3,3, tetramethyl-cyclopropane carboxylate (Knoxthrin, Sumitomo Chemical Co.)

improthrin: 2,4-dioxo-1-(prop-2-inyl)-imidazolidin-3-yl methyl (IR)-cis/trans-chrysanthemat (Pralle, Sumitomo Chemical Co.)

ethofenprox: 2-(4-ethoxyphenyl)-2-methyl propyl-3-phenoxybenzyl ether (Trebon)

Also, listed below are illustrative for other chemicals that may be used as insecticides, rejectant, potency intensifiers and growth control agents.

acetamiprid: N'-[(6-chloro-3-pyridyl)methyl]-N²-cyano-N'-methyl acetone amidine (Mospilan)

diazinon: (2-isopropyl-4-methyl pyrimidil-6)-diethyl thiophosphate (Diazinon)

fenitrothion, MEP: O,O-dimethyl-O-(3-methyl-4-nitrophenyl) thiophosphate (Sumithion)

pyridaphention: O,O-dimethyl-O-(3-oxo-2-phenyl-2H-pyridazin-6-yl)phosphothioate (Ofunack)

malathion: dimethyl dicarbetoxy ethyl dithiophosphate (Malathon)

imidacloprid: 1-(6-chloro-3-pyridyl methyl)-N-nitro imidazolidin-2-ylideneamine (Admire)

dichlorvos: O,O-dimethyl O-(2,2-dichloro) vinylphosphate (DDVP)

benzil benzoate isobornyl thiocyanoacetate (IBTA)

dehydro acetate piperonyl butoxide (P. B.)

paraoxy benzoic acid phenyl salicylate

S-421

N-(2-ethyl hexyl)-bicyclo[2,2,1]-hepta-5-ene-2,3-dicarboxy imid (Synepirin 222)

N,N-diethyl-m-toluamid (Deet)

Pyriproxyfen: 4-phenoxy phenyl (RS)-2-(2-pyridyl oxy) propyl ether (Sumilarv)

Next, mention is made of usable materials for chemical carrier or impregnable particles or particulate mass. Illustrative are, for example, viscose, linter and inorganic substances such as calcium silicate. Alternatives may be porous bodies formed as row materials synthetic fibers such as of polypropylene and they may also be activated carbon. Among them, a plant derived material such as pulp, viscose or linter is most preferred as a raw material for chemical carrier or impregnable particle or particulate material in view of their specific gravity and chemical carrying capacity. Such materials which are commercially available include foamed cellulose beads made of pulp and viscose as main raw materials and supplied from Rengo, K. K. under the trade name of Viscopar (spelled phonetically).

Promoting agitation of the chemical impregnated carrier particles as mentioned above requires them to be light weighted being lower in specific gravity. Their receptacle is preferably made of plastic which is by nature electrically nonconductive, light weighted and also economical. However, plastic by frictional or rubbing contact tends to bear electrostatic charges and once charged to be hard to set them free. Therefore, it is possible for the chemical carrier particles which are lower in specific gravity, when stirred to impede the agitation and thus to become detrimental to energy efficiency. It is thus desirable to apply an anti-static treatment to the chemical carrier particles and preferably to their receptacle as well. A typical plastic anti-static treatment widely method is by an additive and to this end makes use of a surface active agent. In such methods, an anti-static agent may be coated on the surfaces of a plastic (surface coating method) or alternatively be mixed into a plastic body (mixing method). Such agents are anionic, cationic, nonionic or bipolar ionic active agents suitably adapted to the methods. A variety of chemicals having a surfactant as their principal ingredient are commercially available. Examples are "Sanstat AA", "Sanstat 2012A" and "Sanstat 249" made by Sanyo Chemical Industries Ltd., and "Colcoat SP-2001" and "Colcoat SP-2002" featuring the transparency as nonductive coating" made by Colcoat, K. K (all spelled phonetically).

For purposes of the present invention, it is also possible to use one or more of an anti-oxidizing agent, an ultraviolet absorbing agent, an aromatic, a deodorant and so forth to add a stability enhancing efficacy, synergistic efficacy and bells and whistles.

Where it is desired for a chemical which is less volatile to be volatilized effectively, a method is conceivable which is designed to promote volatilization by heating the carrier particle receptacle, the fan itself or any peripheral member.

EXAMPLE 1

On the side to the square blow outlet of 8 cm side of a DC brushless axial fan motor made by K. K. Siko Giken, there was placed a chemical containing cylindrical cartridge of 18 cm inner diameter and 10 cm high with its top bottom covered with nets. The cartridge accommodated therein a mass of 2 grams in weight of particles of 2 mm diameter constituted by foamed cellulose beads, impregnated with 300 milligrams of prallethrin. The apparatus in operation was cyclically turned on and off with an on time of 12 hours and an off time of 12 hours and with the cycle repeated 30 times. Changes with time in the amount of volatilization measured of the chemical and are plotted in the graph shown in FIG. 10. The knock-down potency against common house mosquitoes also measured is shown in Table 4. It should be noted here that the amount of volatilization is indicated by a value per unit time (hour) calculated from the chemical residue that was extracted from the chemical impregnated particulate mass and measured at a given time interval. The potency or efficaciousness is represented by results of tests conducted in a 8 straw mat (13.2 m²) size closed space at a constant temperature of 25° C.

Figure 11:
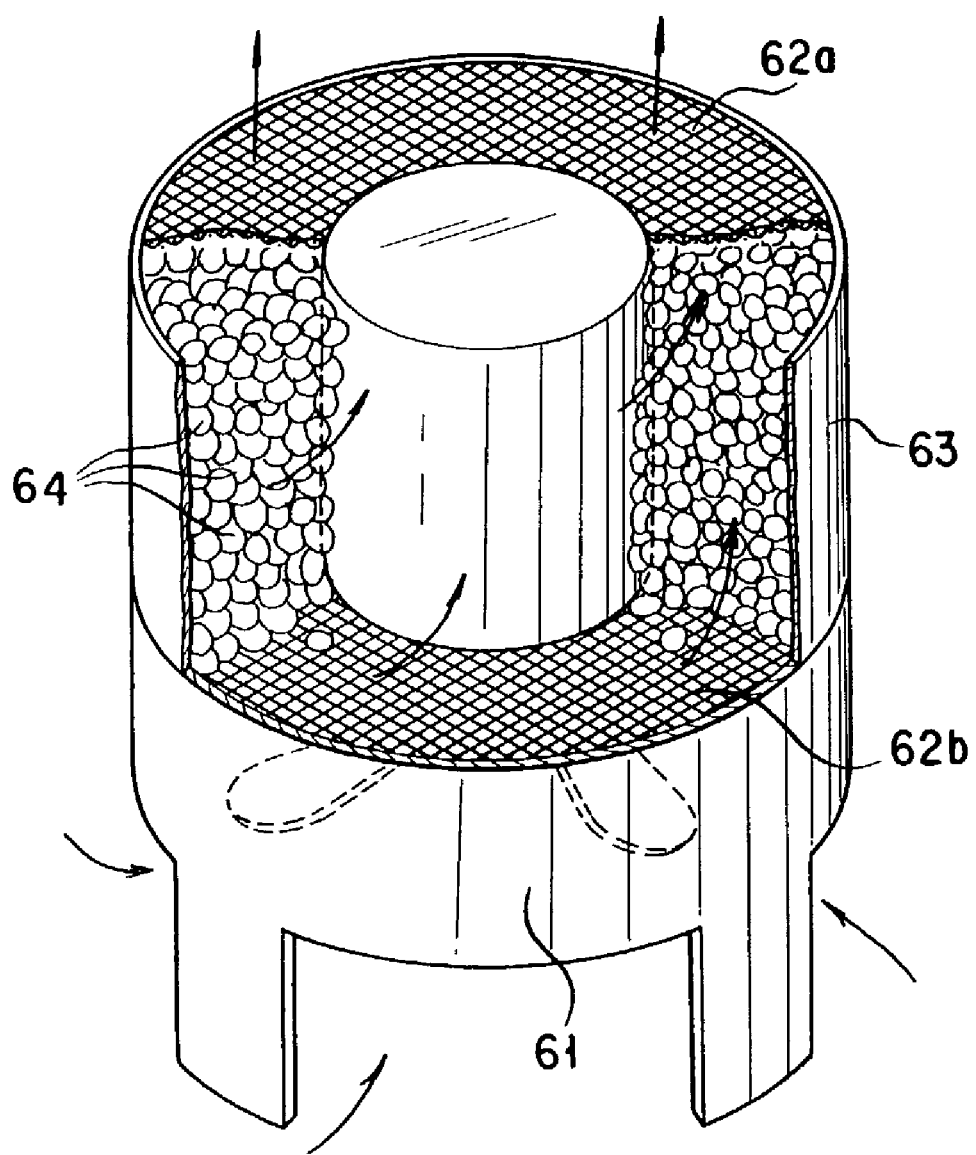
FIG. 11 is a perspective view that diagrammatically depicts a means for volatilizing a chemical from a mass of granules impregnated with the chemical forming a chemical impregnated body according to the present invention.

The apparatus used in this Example had a fan motor mounted therein and a construction in which as shown in FIG. 11 a body portion 61 had a blow outlet (not indicated in the Figure) top-open on which a particulate mass accommodating receptacle 63 was mounted with its top and bottom covered with nets 62a and 62b. In operation, as the fan is rotated, winds blow up from the net 62b of the bottom of the receptacle 63 to fluidize the particulate mass, indicated by discrete particles 64, accommodated therein and in the meantime to permit the chemical impregnated in the mass to volatilize and then to diffuse through the upper net 62a into the outside together with the winds.

EXAMPLE 2

Figure 10:
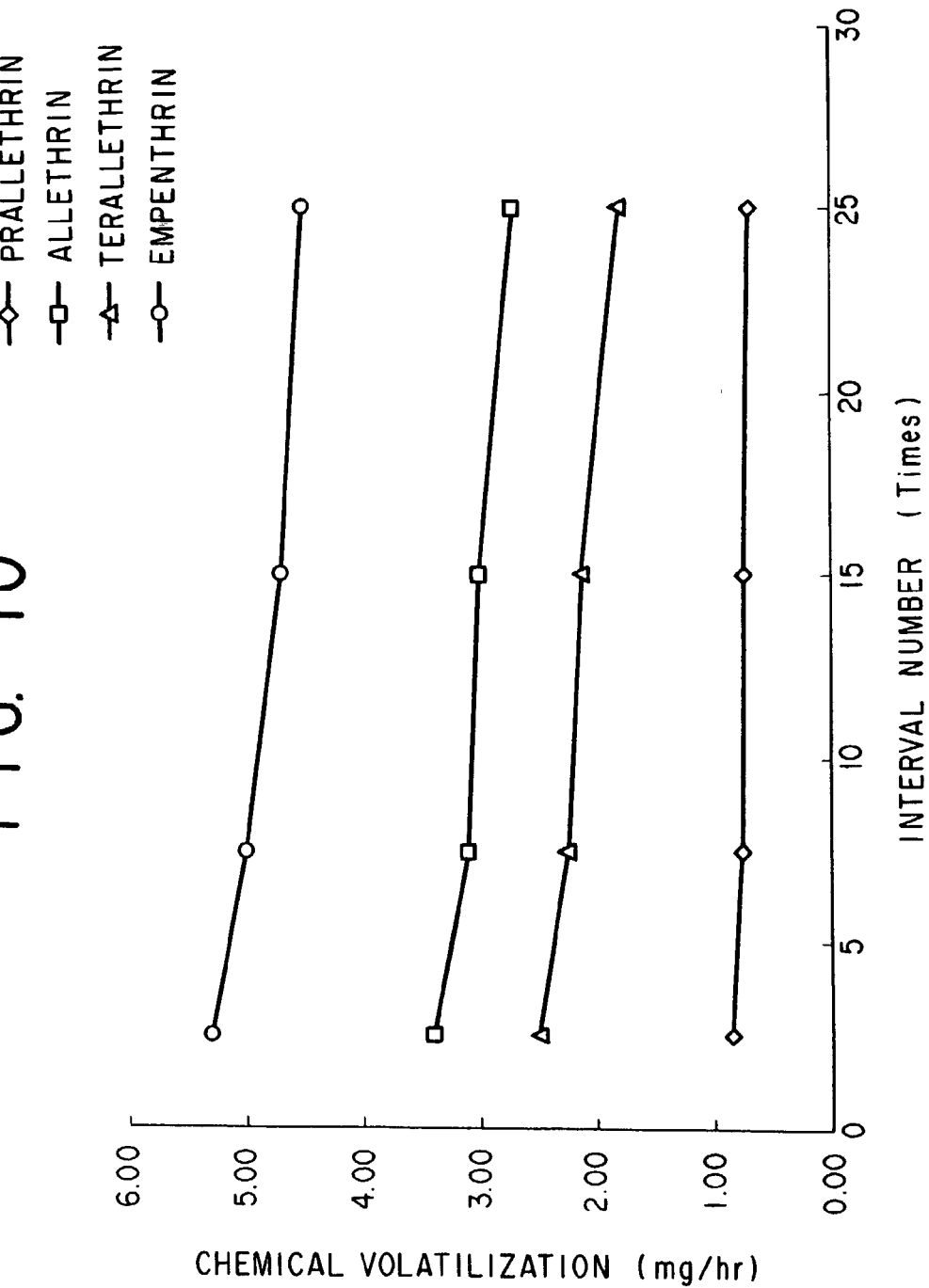
FIG. 10 is a graph in which the rates of chemical volatilization from a chemical impregnated body when impregnated with different chemicals are plotted with respect to a time parameter.

Using the same apparatus, a test was conducted in which the particulate mass was again a mass of 2 grams in weight of foamed cellulose beads of 2 mm diameter which in this example was impregnated with 1200 milligrams of allethrin. Under the same test conditions as in Example 1, changes in the volume of volatilization of the chemical and the knock-down potency for common house mosquitoes were measured. Results of the test are shown in FIG. 10 and Table 11.

EXAMPLE 3

Using the same apparatus, a test was conducted in which the particulate mass was a mass of 2 grams in weight of foamed cellulose beads of 4 mm diameter which in this example was impregnated with 1000 milligrams of terallethrin. Under the same test conditions as in Example 1, changes in the volume of volatilization of the chemical and the knock-down potency for common house mosquitoes were measured. Results of the test are shown in FIG. 10 and Table 11.

EXAMPLE 4

Using the same apparatus, a test was conducted in which the particulate mass was a mass of 2 grams in weight of foamed cellulose beads of 4 mm diameter which in this example was impregnated with 2000 milligrams of empenthrin. Under the same test conditions as in Example 1, changes in the volume of volatilization of the chemical and the knock-down potency for common house mosquitoes were measured. Results of the test are shown in FIG. 10 and Table 11.

TABLE 11

| Chemical Indentification | Amount of Chemical (mg/2 g) | Chemical Impregnated Particles Diameter (mm) | Knock-down Efficacy $KT_{50}$ (min) | | |
|---|---|---|---|---|---|
| | | | 1-st | 15-th | 30-th |
| prallethrin | 300 | 2 | 2.33 | 2.57 | 2.74 |
| allethrin | 1200 | 2 | 2.52 | 2.84 | 3.04 |
| terallethrin | 1000 | 4 | 3.06 | 3.79 | 4.23 |
| empenthrin | 2000 | 4 | 5.29 | 5.33 | 5.47 |

As mentioned previously, an apparatus according to the present invention permits a volatile chemical having insecticide, rejectant or growth control function to be diffused and dispersed stably by a wind force over a prolonged period of time for a variety of noxious or harmful insects, regardless of the vapor pressure the chemical possesses and the amount of volatilization the chemical is aimed for.

Although the present invention has been described hereinbefore in terms of the presently preferred forms of embodiments with respect to or embodied in a fan type chemical diffusing apparatus of volatilizing a chemical, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as compassing all alterations, modifications, or alternative applications as fall within the true spirit and scope of the invention.

What is claimed is:

1. A fan type chemical diffusing apparatus, comprising:
an apparatus main body having an air inlet and an air outlet;
a fan type blower disposed in said apparatus main body and including a motor, a fan comprising a rotary disk and a plurality of blades fastened to a peripheral portion of the rotary disk and provided with an annular hollow space that is on an interior of the fan and surrounded by the blades, and a fan casing surrounding the fan; and
an annular active ingredient impregnated body or mass, for containing an active ingredient, which is disposed in said annular hollow space and separated from said fan and is detachably fixed directly to said fan casing; and
wherein said fan type blower is operable to send air from said air inlet through said hollow space and out through said air outlet.

2. A fan type chemical diffusing apparatus as set forth in claim 1, wherein said active ingredient impregnated body or mass is removably mounted in said hollow space.

3. A fan type chemical diffusing apparatus as set forth in claim 1, wherein said active ingredient impregnated body or mass comprises a mass of discrete particles impregnable with said active ingredient, and said particles each have a shape such that a maximum area of contact of one of the particles with another is not larger than one half of a total surface area thereof.

4. A fan type chemical diffusing apparatus as set forth in claim 1, wherein said active ingredient impregnated body or mass comprises a mass of discrete particles impregnable with said active ingredient, and said particles have a real volume which, as expressed by [apparent volume×(1-percentage of void or voids/100)], ranges from $5\times10^{-5}$ to $5\times10^5$ mm³ per particle.

5. A fan type chemical diffusing apparatus as set forth in claim 1, wherein said fan type blower is adapted to send air into, through and out of an active ingredient impregnated body or mass receptacle that accommodates the active ingredient impregnated mass or body, which comprises a mass of discrete particles with an air flow therethrough ranging between 0.01 and 1.0 m³/min, and said particles then have a specific gravity ranging between 0.005 and 0.5.

6. A fan type chemical diffusing apparatus as set forth in claim 1, wherein at least one of said active ingredient impregnated body or mass and a receptacle therefor is pre-treated for an antistatic.

7. A fan type chemical diffusing apparatus as set forth in claim 1, wherein at least a portion of a casing of the active ingredient impregnated mass or body is made of plastic comprising at least one of: polyester, polypropylene, polyvinyl chloride, ABS, polystyrene, AS, methacrylate resin, polyvinyl alcohol, EVA, phenol resin, silicone resin, polyamide resin, polyacetal resin, polycarbonate resin and thermoplastic polyester resin.

8. A fan type chemical diffusing apparatus as set forth in claim 1, wherein an end point making method for said active ingredient impregnated body or mass is a method of using a lipophilic anthraquinone dye for the impregnated body if hydrophilic and utilizing the phenomena that the color of the dye if dissolved in the chemical is recognizable and that when the chemical is evaporated out the dye gets into the body to make its color unrecognizable.

9. A fan type chemical diffusing apparatus as set forth in claim 1, wherein an end point making method for said active ingredient impregnated body or mass is a method of utilizing a color changeable pigment made of a color changeable electron releasing organic compound and a desensitizer.

10. A fan type chemical diffusing apparatus as set forth in claim 1, wherein an end point making method for said active ingredient impregnated body or mass is a method of utilizing a color changeable electron releasing organic compound, a desensitizer and a color developer.

11. A fan type chemical diffusing apparatus as set forth in claim 1, wherein an end point making method for said active ingredient impregnated body or mass is a method in which the rate of sublimation of a subliming agent is made substantially equal to the rate of volatilization of the chemical.

* * * * *